US012747202B2

(12) United States Patent
Jukei et al.

(10) Patent No.: US 12,747,202 B2
(45) Date of Patent: Sep. 29, 2026

(54) PHOTOSENSITIVE RESIN COMPOSITION, CURED FILM, ELECTRONIC COMPONENT, ANTENNA ELEMENT, SEMICONDUCTOR PACKAGE, AND COMPOUND

(71) Applicant: TORAY INDUSTRIES, INC., Tokyo (JP)

(72) Inventors: Masaya Jukei, Otsu (JP); Hisashi Ogasawara, Otsu (JP); Hitoshi Araki, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 599 days.

(21) Appl. No.: 18/268,411

(22) PCT Filed: Jan. 11, 2022

(86) PCT No.: PCT/JP2022/000472
§ 371 (c)(1),
(2) Date: Jun. 20, 2023

(87) PCT Pub. No.: WO2022/163335
PCT Pub. Date: Aug. 4, 2022

(65) Prior Publication Data

US 2024/0045329 A1 Feb. 8, 2024

(30) Foreign Application Priority Data

Jan. 26, 2021 (JP) ................................ 2021-010013

(51) Int. Cl.
*C07C 275/14* (2006.01)
*G03F 7/028* (2006.01)
(Continued)

(52) U.S. Cl.
CPC ............ *C07C 275/14* (2013.01); *G03F 7/028* (2013.01); *G03F 7/032* (2013.01); *H10W 44/20* (2026.01);
(Continued)

(58) Field of Classification Search
CPC .......... G03F 7/004; G03F 7/027; G03F 7/032; C07C 275/14
See application file for complete search history.

(56) References Cited

U.S. PATENT DOCUMENTS 5,436,112 A * 7/1995 Hsieh ...................... G03F 3/106 430/257
6,281,314 B1 8/2001 Tong et al.
(Continued)

FOREIGN PATENT DOCUMENTS

GB 1580864 A * 12/1980 ................ C08F 2/48
JP 53-285 A 1/1978
(Continued)

OTHER PUBLICATIONS

English translation of Korean Office Action for Korean Application No. 10-2023-7022200, dated Aug. 8, 2025.
(Continued)

*Primary Examiner* — Sophie Hon
(74) *Attorney, Agent, or Firm* — Birch, Stewart, Kolasch & Birch, LLP

(57) ABSTRACT

The purpose of the present invention is to provide a photosensitive resin composition and compound having a low dissipation factor when made into a cured film.
The present invention is a photosensitive resin composition containing (A) a polyfunctional monomer, (B) a binder resin, and (C) a photopolymerization initiator, the (A) polyfunctional monomer containing a compound represented by expression (1) and/or a compound represented by
(Continued)

expression (2), and the (B) binder resin containing one or more substances selected from the group consisting of a polyimide, a polyimide precursor, a polybenzoxazole, a polybenzoxazole precursor, a polyamide, a copolymer thereof, a polyurea, a polyester, a polysiloxane, an acrylic resin, a phenol resin and a benzocyclobutene resin, and a maleic acid resin and a cycloolefin polymer.

13 Claims, 1 Drawing Sheet

(51) Int. Cl.

| | |
|---|---|
| ***G03F 7/032*** | (2006.01) |
| ***H10W 44/20*** | (2026.01) |
| ***H10W 70/685*** | (2026.01) |
| ***H10W 70/69*** | (2026.01) |
| ***H10W 74/10*** | (2026.01) |
| ***H10W 74/47*** | (2026.01) |

(52) U.S. Cl.
CPC ......... *H10W 70/685* (2026.01); *H10W 70/69* (2026.01); *H10W 74/127* (2026.01); *H10W 74/47* (2026.01); *H10W 44/248* (2026.01)

(56) References Cited

U.S. PATENT DOCUMENTS

| | | | |
|---|---|---|---|
| 2005/0272888 | A1 | 12/2005 | Dershem et al. |
| 2018/0210337 | A1 | 7/2018 | Wakita et al. |
| 2018/0327530 | A1 | 11/2018 | Wakita et al. |

FOREIGN PATENT DOCUMENTS

| | | | |
|---|---|---|---|
| JP | 10-500782 | A | 1/1998 |
| JP | 11-293146 | A | 10/1999 |
| JP | 2000-119335 | A | 4/2000 |
| JP | 2008-501826 | A | 1/2008 |
| WO | WO 2017/030070 | A1 | 2/2017 |
| WO | WO 2017/090559 | A | 6/2017 |
| WO | WO 2018/066395 | A1 | 4/2018 |

OTHER PUBLICATIONS

International Search Report, issued in PCT/JP2022/000472, PCT/ISA/210, dated Mar. 22, 2022.

Written Opinion of the International Searching Authority, issued in PCT/JP2022/000472, PCT/ISA/237, dated Mar. 22, 2022.

* cited by examiner

PHOTOSENSITIVE RESIN COMPOSITION, CURED FILM, ELECTRONIC COMPONENT, ANTENNA ELEMENT, SEMICONDUCTOR PACKAGE, AND COMPOUND

TECHNICAL FIELD

The present invention relates to a photosensitive resin composition, a cured film, an electronic component, an antenna element, a semiconductor package, and a compound. More specifically, the present invention relates to a photosensitive resin composition to be used suitably for a surface protective film and an interlayer insulating film in an electronic component of a semiconductor element and the like, an insulating layer of an organic electroluminescent element, and the like.

BACKGROUND ART

Examples of typical materials of the surface protective film and the interlayer insulating film of the semiconductor element, an insulating layer of an organic electrolytic element, and a planarization film of a TFT substrate include polyimide-based resins excellent in heat resistance, electrical insulation, and the like. Furthermore, in order to improve the productivity, a polyimide to which negative-type or positive-type photosensitivity is imparted, a precursor thereof, and the like have also been studied.

In recent years, with expansion of uses and improvement in performance of semiconductors, efforts have been made to reduce costs and increase integration by improving the efficiency of production processes. Thereupon, attention has been focused on a semiconductor device that forms a multilayer metal redistribution layer. Such an insulation film of the multilayer metal redistribution layer requires a plurality of high-temperature treatment processes in the production processes. Further, patternability by photolithography is required for improving productivity. Furthermore, in high-frequency communication device uses for high-speed wireless communication, reduction of a dissipation factor in an insulation film is required in order to reduce a transmission loss. Therefore, high mechanical properties, heat resistance, patternability, and low dissipation factor are required. Examples of the insulation film having sufficient heat resistance include a resin composition containing a resin such as polyimide or polybenzoxazole and a thermal crosslinking agent (Patent Document 1). Examples of methods for imparting patternability include a polyimide precursor in which a specific chemical structure is introduced into a side chain (Patent Document 2).

PRIOR ART DOCUMENTS

Patent Documents

Patent Document 1: Japanese Patent Laid-open Publication No. 2007-16214

Patent Document 2: Japanese Patent Laid-open Publication No. 2011-59656

SUMMARY OF THE INVENTION

Problems to be Solved by the Invention

When a conventional technique is applied as a multilayer wiring insulating film for a high-frequency communication device for high-speed wireless communication, for example, cured films of compositions described in Patent Document 1 and Patent Document 2 have insufficient reduction in dissipation factor.

Solutions to the Problems

In order to solve the problems described above, the present invention relates to the following.

A photosensitive resin composition including a polyfunctional monomer (A), a binder resin (B), and a photopolymerization initiator (C), wherein the polyfunctional monomer (A) contains a compound represented by expression (1) and/or a compound represented by expression (2), and the binder resin (B) contains one or more substance selected from the group consisting of polyimides, polyimide precursors, polybenzoxazoles, polybenzoxazole precursors, polyamides, copolymers thereof, polyurea, polyester, polysiloxane, an acrylic resin, a phenol resin, a benzocyclobutene resin, a maleic acid resin, and a cycloolefin polymer.

[Chem. 1]

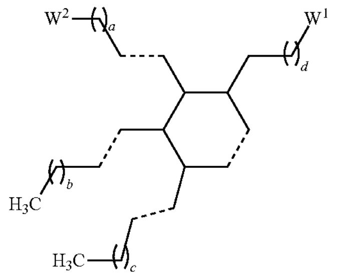

(1)

In expression (1), $W^1$ and $W^2$ each independently represent a monovalent organic group having a carbon-carbon double bond and 2 to 25 carbon atoms. In expression (1), a, b, c, and d are natural numbers each independently satisfying a+b=6 to 17 and c+d=8 to 19, and a broken line part means a carbon-carbon single bond or a carbon-carbon double bond.

[Chem. 2]

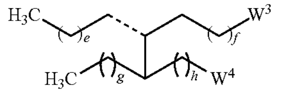

(2)

In expression (2), $W^3$ and $W^4$ each independently represent a monovalent organic group having a carbon-carbon double bond and 2 to 25 carbon atoms. In expression (2), e, f, g, and h are each independently a natural number satisfying e+f=5 to 16 and g+h=8 to 19, and the broken line part means a carbon-carbon single bond or a carbon-carbon double bond.

As another aspect for solving the problem above, the present invention relates to the following.

A compound represented by expression (1) or a compound represented by expression (2).

[Chem. 3]

(1)

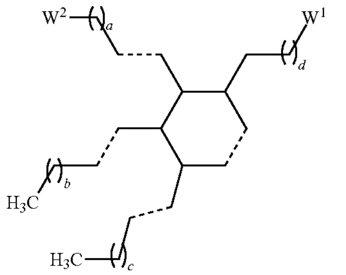

In expression (1), $W^1$ and $W^2$ each independently represent groups represented by expression (3) or expression (4). In expression (1), a, b, c, and d are natural numbers each independently satisfying a+b=6 to 17 and c+d=8 to 19, and a broken line part means a carbon-carbon single bond or a carbon-carbon double bond.

[Chem. 4]

(2)

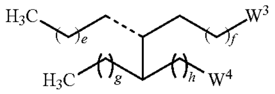

In expression (2), $W^3$ and $W^4$ each independently represent groups represented by expression (3) or expression (4). In expression (2), e, f, g, and h are each independently a natural number satisfying e+f=5 to 16 and g+h=8 to 19, and the broken line part means a carbon-carbon single bond or a carbon-carbon double bond.

[Chem. 5]

(3)

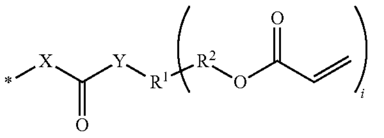

(4)

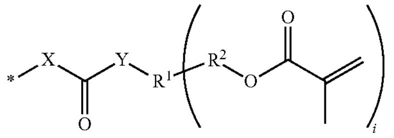

In expression (3) and expression (4), X and Y represent —NH—. $R^1$ represents a single bond or a 2 to 6 valent organic group having 1 to 5 carbon atoms. $R^2$ represents a single bond or a divalent organic group having 1 to 5 carbon atoms. i represents an integer 1 to 5. A sign of * indicates a point of bonding.

Effects of the Invention

A cured film of the photosensitive resin composition of the present invention and a cured film of the composition containing the compound of the present invention are excellent in low dissipation factor.

EMBODIMENTS OF THE INVENTION

Figure 1:
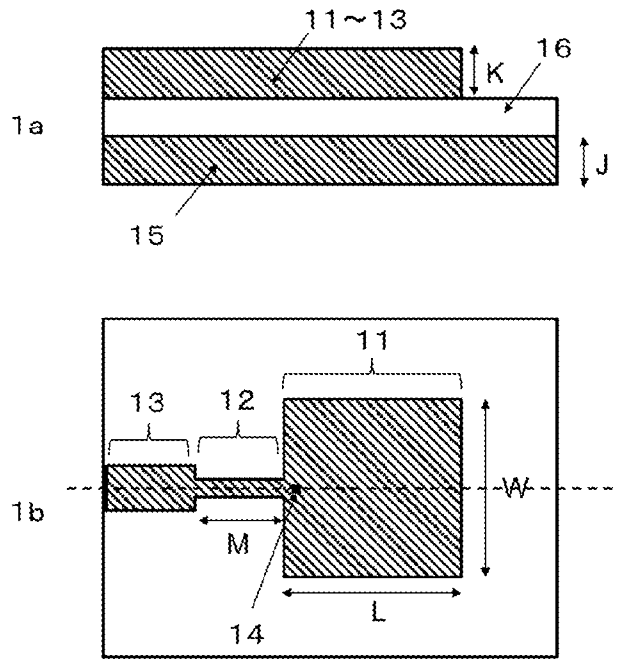
FIG. 1 is a schematic view of a coplanar feeding type microstrip antenna.

The photosensitive resin composition of the present invention contains a polyfunctional monomer (A) (hereinafter, may be omitted as a component (A)), a binder resin (B) (hereinafter, may be omitted as a component (B)), and a photopolymerization initiator (C) (hereinafter, may be omitted as a component (C)), wherein the component (A) contains a compound represented by expression (1) and/or a compound represented by expression (2), and the component (B) contains one or more substance selected from the group consisting of polyimides, polyimide precursors, polybenzoxazoles, polybenzoxazole precursors, polyamides, copolymers thereof, polyurea, polyester, polysiloxane, an acrylic resin, a phenolic resin, and a benzocyclobutene resin, a maleic acid resin, and a cycloolefin polymer.

[Chem. 6]

(1)

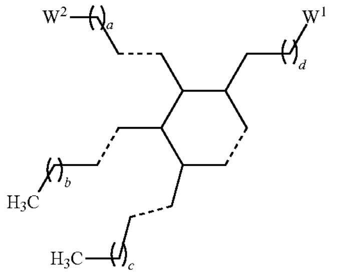

In expression (1), $W^1$ and $W^2$ each independently represent a monovalent organic group having a carbon-carbon double bond and 2 to 25 carbon atoms. In expression (1), a, b, c, and d are natural numbers each independently satisfying a+b=6 to 17 and c+d=8 to 19, and a broken line part means a carbon-carbon single bond or a carbon-carbon double bond.

[Chem. 7]

(2)

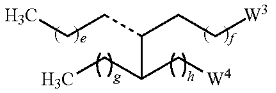

In expression (2), $W^3$ and $W^4$ each independently represent a monovalent organic group having a carbon-carbon double bond and 2 to 25 carbon atoms. In expression (2), e, f, g, and h are each independently a natural number satisfying e+f=5 to 16 and g+h=8 to 19, and the broken line part means a carbon-carbon single bond or a carbon-carbon double bond.

The photosensitive resin composition of the present invention contains the component (A). By containing the component (A), the component (C) causes a crosslinking reaction with an active species generated by exposure, and a negative pattern is obtained. Further, the cured film obtained by curing the photosensitive composition has a low dielectric constant and a low dissipation factor.

The component (A) contains a compound represented by expression (1) and/or a compound represented by expression (2). The compound represented by expression (1) and/or the compound represented by expression (2) is a photopolymerizable monomer, and is obtained by a reaction of a dimer acid or a derivative thereof with a compound having a carbon-carbon double bond.

The dimer acid is a known dibasic acid obtained by an intermolecular polymerization reaction of an unsaturated fatty acid, and is obtained by dimerizing an unsaturated fatty acid having 11 to 22 carbon atoms. The dimer acid industrially obtained is mainly composed of a dibasic acid having 36 carbon atoms obtained by dimerizing an unsaturated fatty acid having 18 carbon atoms such as oleic acid or linoleic acid, but may contain an arbitrary amount of a monomeric acid having 18 carbon atoms, a trimer acid having 54 carbon atoms, and another polymerized fatty acid having 20 to 54 carbon atoms depending on a degree of purification.

Examples of the dimer acid derivative include dimer diols in which all carboxyl groups of the dimer acid are primary hydroxy groups, dimer diamines in which all carboxyl groups are primary amino groups, dimer thiols in which all carboxyl groups are primary thiol groups, and dimer isocyanates in which all carboxyl groups are isocyanate groups. Furthermore, examples thereof include an epoxy compound and an oxetane compound obtained by reacting these functional groups.

The compound having a carbon-carbon double bond further contains one functional group capable of reacting with the dimer acid derivative. Specific examples of the functional group include an amino group, a hydroxy group, a carboxyl group or a substituent of a salt thereof, an epoxy group, an acid anhydride group, and an isocyanate group. A compound represented by expression (1) and/or a compound represented by expression (2) is obtained by a reaction between these functional groups and a functional group of the dimer acid or a derivative thereof.

Specific examples of the compound having a carbon-carbon double bond include alcohols having one ethylenically unsaturated bond and one hydroxyl group, such as N-(4-aminophenyl)maleimide, 4-aminostyrene, 3-aminostyrene, 2-aminostyrene, 3-amino-1-propene, 2-hydroxyethyl (meth)acrylate, 2-hydroxypropyl(meth)acrylate, 2-hydroxybutyl(meth)acrylate, 1-(meth)acryloyloxy-2-propyl alcohol, 2-(meth)acrylamide ethyl alcohol, methylol vinyl ketone, 2-hydroxyethyl vinyl ketone, 2-hydroxy-3-methoxypropyl (meth)acrylate, 2-hydroxy-3-butoxypropyl(meth)acrylate, 2-hydroxy-3-phenoxypropyl(meth)acrylate, 2-hydroxy-3-t-butoxypropyl(meth)acrylate, 2-hydroxy-3-cyclohexyl alkoxypropyl(meth)acrylate, 2-hydroxy-3-cyclohexyloxypropyl(meth)acrylate, and 2-(meth)acryloxy ethyl-2-hydroxypropyl phthalate: 2-vinylbenzyl alcohol, 3-vinylbenzyl alcohol, and 4-vinylbenzyl alcohol; alcohols having two or more ethylenically unsaturated bonds and one hydroxyl group, such as glycerin-1, 3-di(meth)acrylate, glycerin-1, 2-di(meth)acrylate, trimethylolpropane di(meth)acrylate, pentaerythritol tri(meth)acrylate, dipentaerythritol penta(meth)acrylate, glycerin-1-allyloxy-3-methacrylate, glycerin-1-allyloxy-2-methacrylate, 2-ethyl-2-(hydroxymethyl)propane-1, 3-diylbis(2-methacrylate), and 2-(acryloyloxy)-2-(hydroxymethyl)butyl methacrylate; and acrylic acid, methacrylic acid, vinyl acetate, and crotonic acid, itaconic acid, maleic acid, fumaric acid, cinnamic acid, and derivatives thereof, acrylic anhydride, methacrylic anhydride, itaconic anhydride, maleic anhydride, 4-pentene-1,2-dicarboxylic anhydride, 5-norbornene-2,3-dicarboxylic anhydride, 2-acryloyloxyethyl isocyanate, 2-methacryloyloxyethyl isocyanate, and 1,1-(bisacryloyloxymethyl)ethyl isocyanate. Here, the “(meth)acrylate” refers to methacrylate or acrylate. The same applies to similar notations.

Specific examples of commercially available products of the dimer acid include HARIDIMER 200, HARIDIMER 270S (the above are trade names, manufactured by Harima Chemicals, Inc.), Td-205 (W), Td-395 (the above are trade names, manufactured by Tsuno Food Industry Co., Ltd.), Pripol 1004, Pripol 1006, Pripol 1009, Pripol 1013, Pripol 1017, and Pripol 1040 (the above are trade names, manufactured by Croda Japan K.K.).

As the dimer acid derivative, commercially available products of dimer diols include Pespol HP-1000 (which is a trade name, manufactured by TOAGOSEI CO., LTD.) and Pripol 2023 (which is a trade name, manufactured by Croda Japan K.K.). Examples of commercially available products of the dimer diamine include Versamine 551, Versamine 552 (the above are trade names of BASF Japan Ltd.), Priamine 1071, Priamine 1073, Priamine 1074, and Priamine 1075 (the above are trade names, manufactured by Croda Japan K.K.).

Further, from a viewpoint of exposure sensitivity, in expression (1) and expression (2), at least one of $W^1$ and $W^2$ and at least one of $W^3$ and $W^4$ are preferably groups represented by expression (3), expression (4), expression (5) or expression (6).

[Chem. 8]

(3)

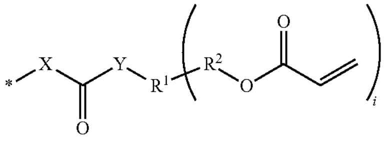

(4)

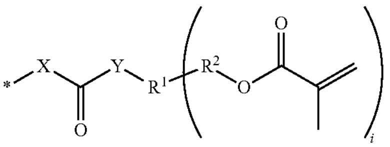

[Chem. 9]

(5)

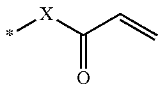

(6)

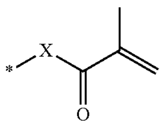

In expression (3), expression (4), expression (5) and expression (6), X and Y each independently represent —NH—, —O—, —$CH_2$— or —S—. $R^1$ represents a single bond or a 2 to 6 valent organic group having 1 to 5 carbon atoms. $R^2$ represents a single bond or a divalent organic group having 1 to 5 carbon atoms. i represents an integer 1 to 5. A sign of * indicates a point of bonding.

Specific examples of the component (A) in which at least one of $W^1$ and $W^2$ and at least one of $W^3$ and $W^4$ are groups represented by expression (3), expression (4), expression (5), or expression (6) in expression (1) and expression (2) include expression (7).

[Chem. 10]
(7)
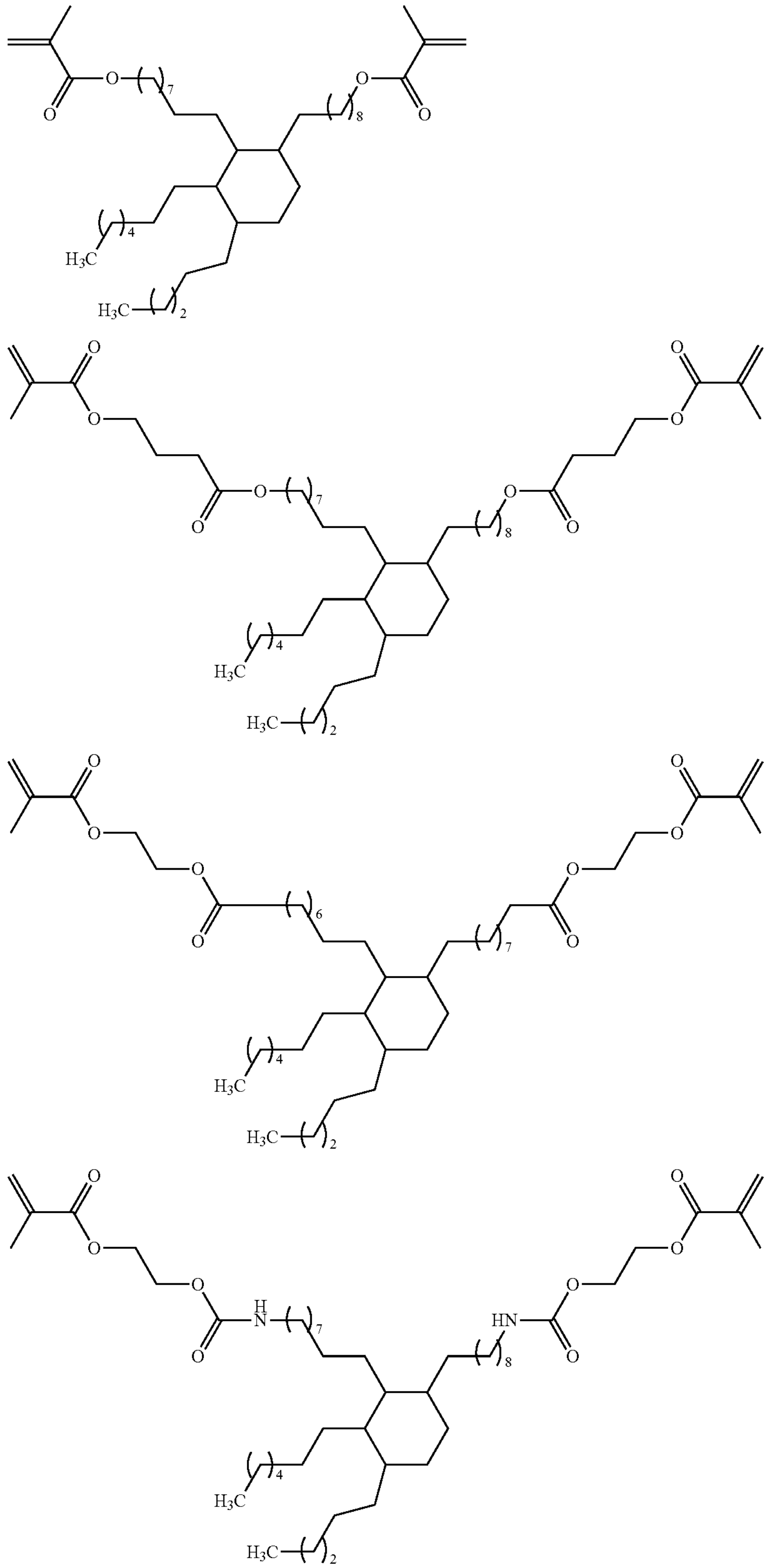

-continued

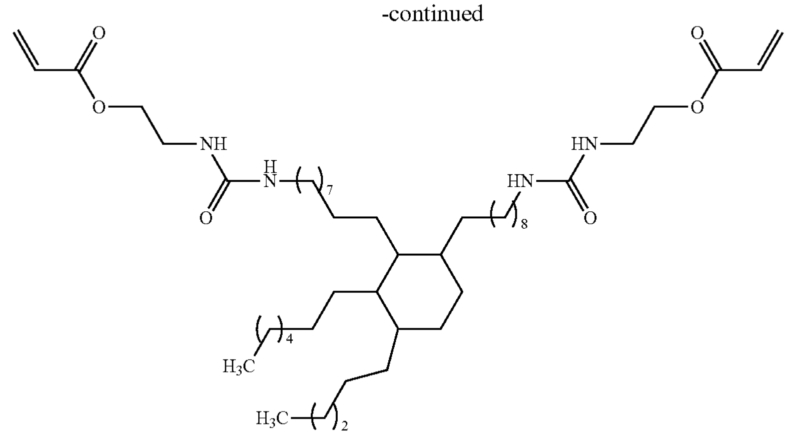

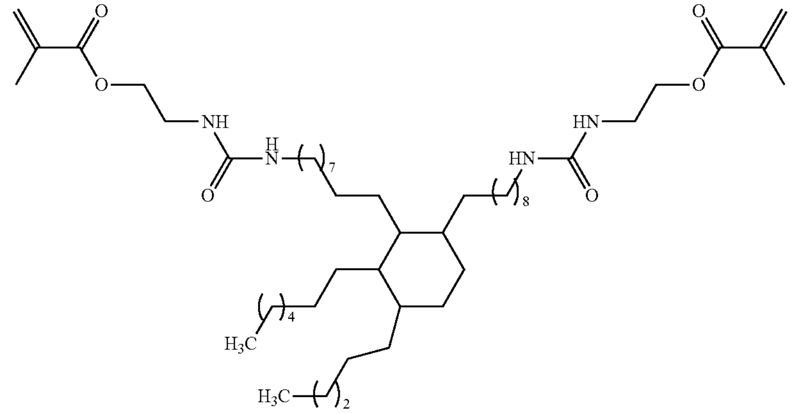

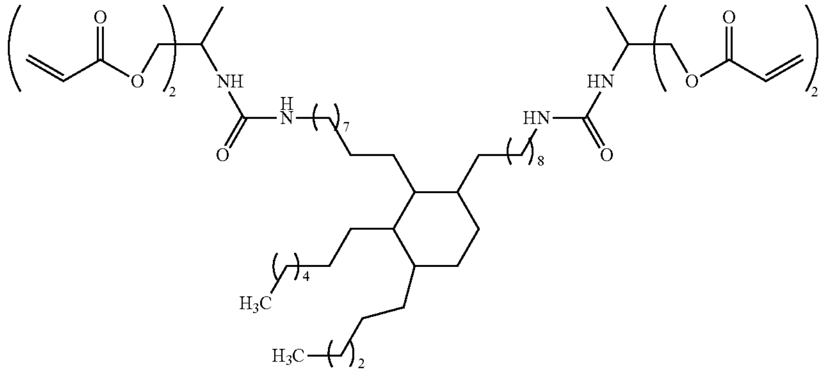

Further, from a viewpoint of reducing dielectric properties, in expression (1) and expression (2), at least one of $W^1$ and $W^2$ and at least one of $W^3$ and $W^4$ is groups represented by expression (3) or expression (4), and in expression (3) and expression (4), X and Y are preferably —NH—.

Further, in expression (1) and expression (2), at least one of $W^1$ and $W^2$ and at least one of $W^3$ and $W^4$ are more preferably groups represented by expression (8), expression (9), expression (10) or expression (11).

[Chem. 11]

(8)

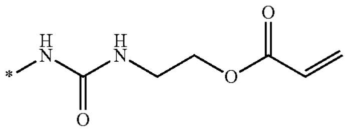

-continued (9)

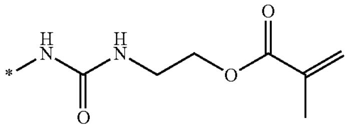

[Chem. 12]

(10)

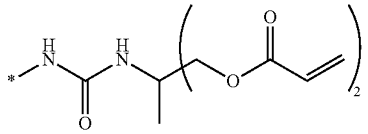

(11)

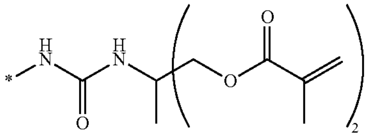

A sign of * indicates a point of bonding.

The component (A) is preferably prepared in a range of 5% by mass or more and 50% by mass or less in the resin composition.

A method for producing the component (A) is not particularly limited, and a known synthesis method such as an addition reaction or a condensation reaction can be adopted. An example of a specific production method will be described below.

As a first step, a compound having one functional group capable of reacting with a carbon-carbon double bond and a dimer acid derivative is charged into a reaction vessel under a nitrogen atmosphere, and stirred. At this time, if necessary, a solvent may be added, and a reaction catalyst or a reaction accelerator may be further added.

As the solvent, one having a solubility parameter of 10 or less in a Fedor method is preferably used. Specific examples thereof include, but are not limited to, toluene, and propylene glycol methyl ether acetate. Further, two or more kinds of solvents may be contained.

The reaction catalyst can be appropriately selected according to a reaction to be applied, and examples of the reaction catalyst include an ammonium-based catalyst such as tetrabutylammonium acetate, an amino-based catalyst such as dimethylbenzylamine, and a phosphorus-based catalyst such as triphenylphosphine in a case of a reaction of a carboxyl group with an epoxy group, and examples of the reaction catalyst include a tin compound such as dibutyltin dilaurate and a tertiary amine such as 1,4-dibicyclo[2.2.2] octane in a case of a reaction of an isocyanate group with an amino group or a hydroxyl group. The reaction accelerator is mainly required in a case where the reaction to be applied is a condensation reaction of a carboxyl group with an amino group or a hydroxyl group, and examples thereof include dicyclohexylcarbodiimide, and diisopropylcarbodiimide, but the reaction accelerator is not limited thereto.

As a second step, the dimer acid derivative is added dropwise to a solution during stirring that has been prepared in the first step, and the mixture is stirred until the reaction is completed. The dimer acid derivative is preferably the aforementioned commercially available product. In a case where a reaction heat is large, cooling may be performed during dropping as necessary.

As a third step, after completion of the reaction, the solvent of a preparation solution is removed with an evaporator to obtain the component (A). Further, in a case where the reaction catalyst or the reaction accelerator is used, the reaction catalyst or the reaction accelerator is preferably removed by liquid separation treatment or silica gel chromatography.

The component (A) in the present invention can be identified using a nuclear magnetic resonance apparatus (NMR) or the like.

NMR is an analysis method in which a material is placed in a strong magnetic field, pulsed radio waves are emitted to molecules in which directions of spins are aligned, nuclear magnetic resonance is performed, and then a signal generated when the molecules return to an original stable state is detected to analyze a molecular structure and the like. A $^{1}$H-NMR spectrum is most often used in NMR analysis, and it is possible to obtain information on the molecular structure, such as environment in which hydrogen atoms are placed from a chemical shift of a peak, the number of hydrogen atoms from an integral value, and influence of adjacent protons from a splitting of the peak. As an example showing characteristic chemical shifts, a peak appears at 1.5 to 2 ppm for the chemical shift of hydrogen bonded to a carbon at an allylic position, 4.5 to 6 ppm for the chemical shift of a hydrogen atom bonded to an alkene, 6 to 9 ppm for the chemical shift of hydrogen bonded to an aromatic ring, and 5 to 11 ppm for the chemical shift of a hydrogen atom bonded to an amide group.

The photosensitive resin composition of the present invention contains the component (B). By appropriately selecting the component (B), characteristics of the photosensitive resin composition and characteristics of the cured film obtained by curing the photosensitive resin composition can be controlled.

The component (B) contains one or more substance selected from the group consisting of a polyimide, a polyimide precursor, a polybenzoxazole, a polybenzoxazole precursor, a polyamide, a copolymer thereof, a polyurea, a polyester, a polysiloxane, an acrylic resin, a phenol resin, a benzocyclobutene resin, a maleic acid resin, and a cycloolefin polymer. Here, the polyamide refers to a polyamide other than the polyimide precursor and the polybenzoxazole precursor unless otherwise specified.

In particular, from a viewpoint of heat resistance and mechanical properties of the cured film, the component (B) preferably contains one or more substance selected from the group consisting of a polyimide, a polyimide precursor, a polybenzoxazole, a polybenzoxazole precursor, a copolymer thereof, and a maleic acid resin. Further, the component (B) preferably contains one or more substance selected from the group consisting of a polyimide, a polyimide precursor, a polybenzoxazole, a polybenzoxazole precursor, and a copolymer thereof.

Furthermore, the component (B) more preferably contains one or more substance selected from the group consisting of a polyimide, a polyimide precursor, a polybenzoxazole, a polybenzoxazole precursor, and a copolymer thereof, which are obtained by polymerizing the dimer acid derivative as a monomer.

Further, since development with an aqueous alkali solution is possible, it is preferable to contain one or more substance selected from the group consisting of a polyimide having a phenolic hydroxyl group in an acid dianhydride residue or a diamine residue, a polyimide precursor, and a copolymer thereof.

Furthermore, from a viewpoint of developability and low dissipation factor, the component (B) more preferably contains a phenol resin having a biphenyl structure that is a rigid structure. A plurality of kinds of these resins may be combined.

Examples of the polyimide precursor include those obtained by reacting a tetracarboxylic acid and a derivative thereof with a diamine and a derivative thereof. As the polyimide precursor, for example, polyamic acid, polyamide acid ester, polyamic acid amide, or polyisoimide can be considered.

Examples of the tetracarboxylic acid and derivatives thereof include 1,2,4,5-benzene tetracarboxylic acid (pyromellitic acid), 3,3',4,4'-biphenyltetracarboxylic acid, 2,3,3',4'-biphenyl tetracarboxylic acid, 2,2',3,3'-biphenyl tetracarboxylic acid, 1,2,5,6-naphthalene tetracarboxylic acid, 1,4,5,8-naphthalene tetracarboxylic acid, 2,3,6,7-naphthalene tetracarboxylic acid, 3,3',4,4'-benzophenone tetracarboxylic acid, 2,2',3,3'-benzophenone tetracarboxylic acid, bis(3,4-dicarboxyphenyl)methane, bis(2,3-dicarboxyphenyl)methane, 1,1-bis (3,4-dicarboxyphenyl)ethane, 1,1-bis (2,3-dicarboxyphenyl)ethane, 2,2-bis(3,4-dicarboxyphenyl) propane, 2,2-bis(2,3-dicarboxyphenyl)propane, 2,2'-bis[4-(3,4-dicarboxyphenoxy)phenyl]propane, 2,2-bis (3,4-dicarboxyphenyl)hexafluoropropane, 2,2-bis(2,3-dicarboxyphenyl)hexafluoropropane, bis(3,4-dicarboxyphenyl)sulfone, bis(3,4-dicarboxyphenyl)ether, 2,3,5,6-pyridine tetracarboxylic acid, or alternatively, 3,4,9,10-perylene tetracarboxylic acid, N,N'-bis[5,5'-hexafluoropropane-2,2-diyl-bis(2-hydroxyphenyl)]bis(3,4-dicarboxybenzoic acid amide), bicyclo[2.2.2]octane-7-ene-2,3,5,6-tetracarboxylic acid, 1,2,4,5-cyclohexanetetracarboxylic acid, 1,2,3,4-cyclopentane tetracarboxylic acid, 1,2,3,4-cyclobutane tetracarboxylic acid, or 2,3,4,5-tetrahydrofuran tetracarboxylic acid, butane-1,2,3,4-tetracarboxylic acid, or their tetracarboxylic acid dianhydrides, tetracarboxylic acid dichlorides or tetracarboxylic acid active diesters. These compounds may be used alone or in combination of two or more.

Examples of the diamine and derivatives thereof include m-phenylenediamine, p-phenylenediamine, 3,5-diaminobenzoic acid, 4,4'-diaminobiphenyl, bis(4-aminophenoxy) biphenyl, 2,2'-dimethyl-4,4'-diaminobiphenyl, 2,2'-diethyl-4,4'-diaminobiphenyl, 3,3'-dimethyl-4,4'-diaminobiphenyl, 3,3'-diethyl-4,4'-diaminobiphenyl, 2,2',3,3'-tetramethyl-4,4'-diaminobiphenyl, 3,3',4,4'-tetramethyl-4,4'-diaminobiphenyl, 2,2'-bis(trifluoromethyl)-4,4'-diaminobiphenyl, dimercaptophenylenediamine, 1,5-naphthalenediamine, 2,6-naphthalenediamine, 9,10-anthracenediamine, 4,4'-diaminobenzanilide, 3,4'-diaminodiphenyl ether, 4,4'-diaminodiphenyl ether, 3-carboxy-4,4'-diaminodiphenyl ether, 3-sulfonic acid-4,4'-diaminodiphenyl ether, bis[4-(4-aminophenoxy) phenyl]ether, 1,4-bis(4-aminophenoxy)benzene, 1,3-bis(3-aminophenxy)benzene, 1,3-bis(4-aminophenoxy)benzene, 3,4'-diaminodiphenylmethane, 4,4'-diaminodiphenylmethane, 2,2-bis(4-aminophenyl)hexafluoropropane, 3,3'-diaminodiphenylsulfone, 3,4'-diaminodiphenylsulfone, 4,4'-diaminodiphenylsulfone, bis(4-aminophenoxyphenyl) sulfone, bis(3-aminophenoxyphenyl)sulfone, 2,7-diaminofluorene, 9,9-bis(4-aminophenyl)fluorene, 2-(4-aminophenyl)-5-aminobenzoxazole, 2-(3-aminophenyl)-5-aminobenzoxazole, 2-(4-aminophenyl)-6-aminobenzoxazole, 2-(3-aminophenyl)-6-aminobenzoxazole, 1,4-bis(5-amino-2-benzoxazolyl) benzene, 1,4-bis(6-amino-2-benzoxazolyl)benzene, 1,3-bis (5-amino-2-benzoxazolyl)benzene, 1,3-bis(6-amino-2-benzoxazolyl)benzene, 2,6-bis(4-aminophenyl) benzobisoxazole, 2,6-bis (3-aminophenyl)benzobisoxazole, bis[(3-aminophenyl)-5-benzoxazolyl], bis[(4-aminophenyl)-5-benzoxazolyl], bis[(3-aminophenyl)-6-benzoxazolyl], bis[(4-aminophenyl)-6-benzoxazolyl], 3,4'-diaminodiphenyl sulfide, 4,4'-diaminodiphenyl sulfide, 4-aminobenzoic acid 4-aminophenyl ester, 1,3-bis(4-anilino)tetramethyldisiloxane, ethylenediamine, 1,3-diaminopropane, 2-methyl-1,3-propanediamine, 1,4-diaminobutane, 1,5-diaminopentane, 2-methyl-1,5-diaminopentane, 1,6-diaminohexane, 1,2-cyclohexanediamine, 1,4-cyclohexanediamine, bis(4-aminocyclohexyl)methane, 1,7-diaminoheptane, 1,8-diaminooctane, 1,9-diaminononane, 1,10-diaminodecane, 1,11-diaminoundecane, 1,12-diaminododecane, and dimer diamine. In particular, from a viewpoint of reducing the dissipation factor, dimer diamine is preferable.

Further, in uses where alkali solubility is required, bisaminophenol compounds are preferred. Examples of the bisaminophenol compound include bis(3-amino-4-hydroxyphenyl)ether, bis(3-amino-4-hydroxyphenyl)methylene, bis [N-(3-aminobenzoyl)-3-amino-4-hydroxyphenyl]sulfone, bis[N-(4-aminobenzoyl)-3-amino-4-hydroxyphenyl]-sulfone, bis(3-amino-4-hydroxyphenyl)sulfone, bis(3-amino-4-hydroxyphenyl)propane, 2,2'-bis[N-(3-aminobenzoyl)-3-amino-4-hydroxyphenyl]propane, 2,2'-bis[N-(4-aminobenzoyl)-3-amino-4-hydroxyphenyl]propane, 9,9-bis (3-amino-4-hydroxyphenyl)fluorene, 9,9-bis[N-(3-aminobenzoyl)-3-amino-4-hydroxyphenyl]fluorene, 9,9-bis[N-(4-aminobenzoyl)-3-amino-4-hydroxyphenyl]fluorene, N,N'-bis(3-aminobenzoyl)-2,5-diamino-1,4-dihydroxybenzene, N,N'-bis(4-aminobenzoyl)-2,5-diamino-1,4-dihydroxybenzene, N,N'-bis(4-aminobenzoyl)-4,4'-diamino-3,3-dihydroxybiphenyl, N,N'-bis(3-aminobenzoyl)-3,3'-diamino-4,4-dihydroxybiphenyl, N,N'-bis(4-aminobenzoyl)-3,3'-diamino-4,4-dihydroxybiphenyl, 3,3'-diamino-4,4'-biphenol, bis(3-amino-4-hydroxyphenyl)methane, 1,1-bis (3-amino-4-hydroxyphenyl)ethane, 2,2-bis(3-amino-4-hydroxyphenyl)propane, 2,2-bis(3-amino-4-hydroxyphenyl)hexafluoropropane, or 2,2-bis[3-(3-aminobenzamido)-4-hydroxyphenyl]hexafluoropropane.

Further, examples of the diamine having a siloxane structure include bis(3-aminopropyl)tetramethyldisiloxane and bis(p-aminophenyl)octamethylpentasiloxane, which are preferable because adhesion to a substrate can be improved.

The polyamine compounds above can be used as it is or as compounds in which an amine moiety is isocyanated or trimethylsilylated. Further, these two or more polyamine compounds may be used in combination.

Further, a weight-average molecular weight of resin can be adjusted by sealing a resin terminal with a monoamine, an acid anhydride, an acid chloride, or a monocarboxylic acid.

Preferable examples of the monoamine include 5-amino-8-hydroxyquinoline, 1-hydroxy-7-aminonaphthalene, 1-hydroxy-6-aminonaphthalene, 1-hydroxy-5-aminonaphthalene, 1-hydroxy-4-aminonaphthalene, 2-hydroxy-7-aminonaphthalene, 2-hydroxy-6-aminonaphthalene, 2-hydroxy-5-aminonaphthalene, 1-carboxy-7-aminonaphthalene, 1-carboxy-6-aminonaphthalene, 1-carboxy-5-aminonaphthalene, 2-carboxy-7-aminonaphthalene, 2-carboxy-6-aminonaphthalene, 2-carboxy-5-aminonaphthalene, 2-aminobenzoic acid, 3-aminobenzoic acid, 4-aminobenzoic acid, 4-aminosalicylic acid, 5-aminosalicylic acid, 6-aminosalicylic acid, 3-amino-4,6-dihydroxypyrimidine, 2-aminophenol, 3-aminophenol, 4-aminophenol, 2-aminothiophenol, 3-aminothiophenol, and 4-aminothiophenol. Two or more of these monoamines may be used in combination.

Preferable examples of the acid anhydride, the acid chloride, and the monocarboxylic acid include acid anhydrides such as phthalic anhydride, maleic anhydride, nadic acid anhydride, cyclohexanedicarboxylic acid anhydride, and 3-hydroxyphthalic acid anhydride, monocarboxylic acids such as 3-carboxyphenol, 4-carboxyphenol, 3-carboxythiophenol, 4-carboxythiophenol, 1-hydroxy-7-carboxynaphthalene, 1-hydroxy-6-carboxynaphthalene, 1-hydroxy-5-carboxynaphthalene, 1-mercapto-7-carboxynaphthalene, 1-mercapto-6-carboxynaphthalene, and 1-mercapto-5-carboxynaphthalene, monoacid chloride compounds in which carboxyl groups thereof are converted into an acid chloride, monoacid chloride compounds in which only one carboxyl group of dicarboxylic acids, such as terephthalic acid, phthalic acid, maleic acid, cyclohexanedicarboxylic acid, 1,5-dicarboxynaphthalene, 1,6-dicarboxynaphthalene, 1,7-dicarboxynaphthalene, and 2,6-dicarboxynaphthalene, is converted into an acid chloride, and active ester compounds produced by reacting a monoacid chloride compound with N-hydroxybenzotriazole or N-hydroxy-5-norbornene-2,3-dicarboximide. Two or more of these compounds may be used in combination.

As the polyimide, for example, products obtained by cyclodehydrating a polyamic acid, a polyamide acid ester, a polyamic acid amide, or a polyisoimide mentioned above by a reaction with heat, an acid, a base, etc. can be considered. The polyimide has a tetracarboxylic acid and/or its derivative residue and a diamine and/or its derivative residue.

The polyimide precursor is a thermosetting resin and, when subjected to high-temperature thermosetting and cyclodehydration, forms high heat-resistant imide bonds, thus obtaining a polyimide. Accordingly, by containing in the resin composition the polyimide having high heat-resistant imide bonds, the heat resistance of the cured film obtained can be conspicuously improved. Therefore, the cured film is suitable for use in uses requiring high heat resistance. Further, since the polyimide precursor is a resin that improves in heat resistance after dehydrating cyclization, the resin composition is suitable in the case where the resin composition is used for uses in which it is desired to achieve both favorable characteristics of the precursor structure prior to the dehydrating cyclization and favorable heat resistance of the cured film, and the like.

Examples of the polyimide include a polyimide containing a structural unit represented by the following expression (12).

[Chem. 13]

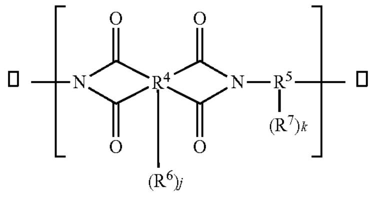

(12)

In expression (12), $R^4$ represents a 4 to 10 valent organic group, and $R^5$ represents a 2 to 8 valent organic group. $R^6$ and $R^7$ each represent a hydroxyl group or an organic group having 1 to 20 carbon atoms, and each may be a single group or a mixture of different groups. j and k represent an integer of 0 to 6. $R^4—(R^6)_j$ represents the aforementioned tetracarboxylic acid and/or a derivative residue thereof. $R^5—(R^7)_k$ represents the aforementioned diamine and/or a derivative residue thereof. In particular, a dimer diamine residue is preferable from a viewpoint of low dissipation factor. A sign of * indicates a point of bonding.

As the polyimide precursor, a polyamic acid or a polyamide acid ester is preferable, and examples thereof include a polyimide precursor containing a structural unit represented by expression (13).

[Chem. 14]

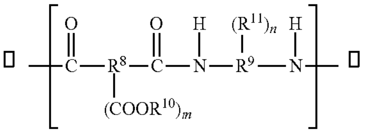

(13)

In expression (13), $R^8$ represents an organic group having a valence of 4 to 6 and $R^9$ represents an organic group having a valence of 2 to 10. A plurality of $R^{11}$ each independently represent an organic group having 1 to 10 carbon atoms or a hydroxyl group, and n represents an integer of 0 to 8. A plurality of $R^{10}$ may be the same or different and represent a hydrogen atom or a monovalent hydrocarbon group having 1 to 30 carbon atoms. m represents an integer 2 to 4. $R^8—(COOR^{10})_m$ represents the aforementioned tetracarboxylic acid and/or a derivative residue thereof. $R^9—(R^{11})_n$ represents the aforementioned diamine and/or a derivative residue thereof. In particular, a dimer diamine residue is preferable from a viewpoint of low dissipation factor. Further, from a viewpoint of solubility in an aqueous alkali solution, a bisaminophenol residue is preferable, and in particular, a 2,2-bis(3-amino-4-hydroxyphenyl)hexafluoropropane residue or a 2,2-bis[3-(3-aminobenzamido)-4-hydroxyphenyl]hexafluoropropane residue is preferable. A sign of * indicates a point of bonding.

Further, when $R^{10}$ represents an organic group having 1 to 30 carbon atoms, $R^{10}$ specifically represents a tetracarboxylic acid diester residue. As a method for producing a tetracarboxylic diester, an acid dianhydride and an alcohol can be directly reacted in a solvent, but it is preferable to use a reaction activator from a viewpoint of reactivity. Examples of a reaction activator include tertiary amines such as pyridine, dimethylaminopyridine, triethylamine, N-methylmorpholine, and 1,8-diazabicycloundecene. An addition amount of the reaction activator is preferably 3 mol % or more and 300 mol % or less, and more preferably 20 mol % or more and 150 mol % or less with respect to the acid anhydride group to be reacted. Further, a small amount of a polymerization inhibitor may be used for a purpose of preventing the ethylenically unsaturated bond moiety from being crosslinked during the reaction. As a result, in the reaction between alcohols having an ethylenically unsaturated bond with low reactivity and a tetracarboxylic acid dianhydride, the reaction can be promoted by heating in a range of 120° C. or lower. Examples of the polymerization inhibitor include phenol compounds such as hydroquinone, 4-methoxyphenol, t-butylpyrocatechol, and bis-t-butylhydroxytoluene. An addition amount of the polymerization inhibitor is preferably 0.1 mol % or more and 5 mol % or less of the phenolic hydroxyl group of the polymerization inhibitor with respect to the ethylenically unsaturated bond of the alcohols.

Examples of the aforementioned alcohols having an ethylenically unsaturated bond include (meth)acrylates having a hydroxyl group and unsaturated fatty acid-modified alcohols. Examples of (meth)acrylate having a hydroxyl group include alcohols each having an ethylenically unsaturated bond and a hydroxyl group, such as 2-hydroxyethyl(meth)acrylate, 2-hydroxypropyl(meth)acrylate, 2-hydroxybutyl (meth)acrylate, 1-(meth)acryloyloxy-2-propyl alcohol, 2-(meth)acrylamide ethyl alcohol, methylol vinyl ketone, 2-hydroxyethyl vinyl ketone, 2-hydroxy-3-methoxypropyl (meth)acrylate, 2-hydroxy-3-butoxypropyl(meth)acrylate, 2-hydroxy-3-phenoxypropyl(meth)acrylate, 2-hydroxy-3-t-butoxypropyl(meth)acrylate, 2-hydroxy-3-cyclohexylalkoxypropyl(meth)acrylate, 2-hydroxy-3-cyclohexyloxypropyl(meth)acrylate, 2-(meth)acryloxyethyl-2-hydroxypropyl phthalate; alcohols having two or more ethylenically unsaturated bonds and one hydroxyl group, such as glycerin-1, 3-di(meth)acrylate, glycerin-1, 2-di(meth)acrylate, trimethylolpropane di(meth)acrylate, pentaerythritol tri(meth)acrylate, dipentaerythritol penta(meth)acrylate, glycerin-1-allyloxy-3-methacrylate, glycerin-1-allyloxy-2-methacrylate, 2-ethyl-2-(hydroxymethyl)propane-1, 3-diylbis(2-methacrylate), and 2-(acryloyloxy)-2-(hydroxymethyl)butyl methacrylate.

Examples of the unsaturated fatty acid-modified alcohols include unsaturated fatty acid-modified alcohols having 6 or more carbon atoms. From a viewpoint of exposure sensitivity, an alcohol having an unsaturated group at the terminal or a double bond having a cis structure is preferable, and from a viewpoint of dielectric constant and dissipation factor, the number of carbon atoms is preferably 12 or more. Specific examples of the unsaturated fatty acid-modified alcohol include 5-hexen-1-ol, 3-hexen-1-ol, 6-heptene-1-ol, cis-5-octene-1-ol, cis-3-octene-1-ol, cis-3-nonene-1-ol, cis-6-nonene-1-ol, 9-decane-1-ol, cis-4-decane-1-ol, 10-undecene-1-ol, 11-dodecane-1-ol, elaidrinoleyl alcohol, oleyl alcohol, linoleyl alcohol, linolenyl alcohol, and erucyl alcohol. Among them, oleyl alcohol, linoleyl alcohol, and linolenyl alcohol are preferable from a viewpoint of dielectric properties and exposure sensitivity of the cured film obtained.

When the acid anhydride is reacted with an alcohol having an ethylenically unsaturated bond, other alcohols may be simultaneously used. Other alcohols can be appropriately selected according to various purposes such as adjustment of exposure sensitivity and adjustment of solubility in an organic solvent. Specific examples thereof include aliphatic alcohols such as methanol, ethanol, 1-propanol, 2-propanol, 1-butanol, 2-butanol, i-butanol, t-butanol, 1-pentanol, 2-pentanol, 3-pentanol, and i-pentanol, and monoalcohols derived from alkylene oxides such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, triethylene glycol monomethyl ether, triethylene glycol monoethyl ether, triethylene glycol monobutyl ether, propylene glycol monomethyl ether, propylene glycol monoethyl ether, propylene glycol monobutyl ether, dipropylene glycol monomethyl ether, dipropylene glycol monoethyl ether, dipropylene glycol monobutyl ether, tripropylene glycol monomethyl ether, tripropylene glycol monoethyl ether, and tripropylene glycol monobutyl ether.

Examples of the polybenzoxazole precursor include polyhydroxyamides obtained by reacting a dicarboxylic acid and a derivative thereof with a bisaminophenol compound or the like as a diamine.

Examples of the dicarboxylic acid include terephthalic acid, isophthalic acid, dimer acid, diphenyl ether dicarboxylic acid, bis(carboxyphenyl)hexafluoropropane, biphenyl dicarboxylic acid, benzophenone dicarboxylic acid, and triphenyl dicarboxylic acid, and examples of tricarboxylic acid include trimellitic acid, trimesic acid, diphenyl ether tricarboxylic acid, and biphenyl tricarboxylic acid. These compounds may be used alone or in combination of two or more. In particular, from a viewpoint of reducing the dissipation factor, the dimer acid is preferable.

Examples of the bisaminophenol include the bisaminophenol compounds exemplified in the polyimide precursor.

The polybenzoxazole precursor is a thermosetting resin and, when subjected to high-temperature thermosetting and cyclodehydration, forms a highly heat-resistant and rigid benzoxazole ring, thus providing a polybenzoxazole. Accordingly, by containing in the resin composition the polybenzoxazole having a highly heat-resistant and rigid benzoxazole ring, the heat resistance of the cured film obtained can be conspicuously improved. Therefore, the cured film is suitable for the case where the cured film is put to uses in which high heat resistance is required, and the like. Further, since the polybenzoxazole precursor is a resin that improves in heat resistance after dehydrating cyclization, the resin composition is suitable in the case where the resin composition is used for uses in which it is desired to achieve both favorable characteristics of the precursor structure prior to the dehydrating cyclization and favorable heat resistance of the cured film, and the like.

Examples of the polybenzoxazole include a polybenzoxazole obtained by cyclodehydrating a dicarboxylic acid and a bisaminophenol compound as a diamine based on a reaction using a polyphosphoric acid, and a polybenzoxazole precursor obtained by cyclodehydrating the polyhydroxyamide by heating or a reaction using a phosphoric anhydride, a base, a carbodiimide compound, or the like.

Examples of the polybenzoxazole include those containing a structural unit represented by expression (14).

[Chem. 15]

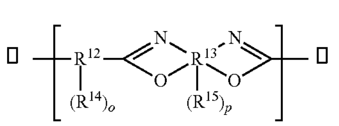

(14)

In expression (14), $R^{12}$ represents an organic group having a valence of 2 to 6, and $R^{13}$ represents an organic group having a valence of 4 to 6. $R^{14}$ and $R^{15}$ each independently represent an organic group having 1 to 10 carbon atoms or a hydroxyl group. o represents an integer of 0 to 4, and p represents an integer of 0 to 2. $R^{12}$—$(R^{14})_o$ represents the aforementioned dicarboxylic acid and/or a derivative residue thereof. In particular, a dimer acid residue is preferable from a viewpoint of low dissipation factor. $R^{13}$—$(R^{15})_p$ represents the aforementioned bisaminophenol compound and/or a derivative residue thereof. A sign of * indicates a point of bonding.

Examples of the polybenzoxazole precursor used in the present invention include those containing a structural unit represented by the following expression (15).

[Chem. 16]

(15)

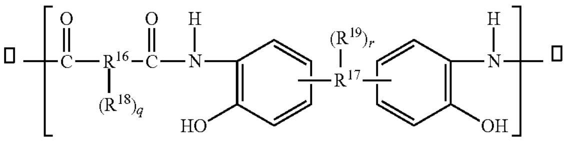

In expression (15), $R^{16}$ represents an organic group having a valence of 2 to 6, and $R^{17}$ represents a single bond or an organic group having a valence of 2 to 6. $R^{18}$ and $R^{19}$ each represent an organic group having 1 to 10 carbon atoms or a hydroxyl group. q and r represent an integer of 0 to 4. $R^{16}$—$(R^{18})_q$ represents the aforementioned dicarboxylic acid and/or a derivative residue thereof. In particular, a dimer acid residue is preferable from a viewpoint of low dissipation factor. $R^{17}$—$(R^{19})_r$ represents the aforementioned bisaminophenol compound and/or a derivative residue thereof. A sign of * indicates a point of bonding.

Examples of the polyamide include those obtained by dehydration condensation of a dicarboxylic acid and a diamine compound based on a reaction using polyphosphoric acid.

Examples of the polyamide include a polyamide containing a structural unit represented by the following expression (16).

[Chem. 17]

(16)

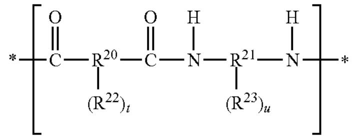

In expression (16), $R^{20}$ and $R^{21}$ represent an organic group having a valence of 2 to 6. $R^{22}$ and $R^{23}$ each independently represent an organic group having 1 to 10 carbon atoms or a hydroxyl group. t represents an integer of 0 to 4, and u represents an integer of 0 to 4. $R^{20}$—$(R^{22})_t$ represents the aforementioned dicarboxylic acid and/or a derivative residue thereof, and $R^{21}$—$(R^{23})_u$ represents a diamine compound excluding the aforementioned bisaminophenol compound and/or a derivative residue thereof. A sign of * indicates a point of bonding.

Further, the component (B) may contain a copolymer composed of two or more substances selected from the group consisting of polyimides, polyimide precursors, polybenzoxazoles, polybenzoxazole precursors, and polyamides.

Examples of the polyurea include those obtained by a polyaddition reaction of a diamine and a polyfunctional isocyanate.

Examples of the diamine include the compounds exemplified for polyimide, polybenzoxazole, and polyamide.

Examples of the polyfunctional isocyanate include hexamethylene diisocyanate, 1,3-bis(isocyanatomethyl)benzene, 1,3-bis(isocyanatomethyl)cyclohexane, norbornene diisocyanate, naphthalene-1,5-disocyanate, diphenylmethane-4,4'-diisocyanate, toluene-2,4-diisocyanate, and the like, and examples of the polyol include ethylene glycol, propylene glycol, pentaerythritol, dipentaerythritol, 1,4-bis(2-hydroxyethoxy)benzene, 1,3-bis(2-hydroxyethoxy)benzene, 4,4'-bis(2-hydroxyethoxy)biphenyl, 2,2-bis(4-(2-hydroxyethoxy)phenyl)propane, and bis(4-(2-hydroxyethoxy)phenyl)methane.

A polyaddition reaction product of a diamine and a polyfunctional isocyanate can be obtained without a catalyst, but a catalyst may be used. Examples of the catalyst include tin compounds such as dibutyltin dilaurate and tertiary amines such as 1,4-diazabicyclo[2.2.2]octane.

As the polyester, a polyester obtained through a polyaddition reaction of a polyol compound and an acid dianhydride is preferable because it is easily synthesized and has few side reactions. As the polyol compound, a compound obtained by a reaction between a polyfunctional epoxy compound and a radical polymerizable group-containing monobasic acid compound such as (meth)acrylic acid is preferable because it is easy to introduce a radical polymerizable group and an aromatic ring.

Examples of the polyfunctional epoxy compound include, but are not limited to, aliphatic epoxy compounds such as ethylene glycol diglycidyl ether, neopentyl glycol diglycidyl ether, or hydrogenated bisphenol-A-diglycidyl ether, or aromatic epoxy compounds such as hydrogenated bisphenol-A-diglycidyl ether or 9,9-bis(4-glycidyloxyphenyl)fluorene.

Further, examples of other polyol compounds include aliphatic alcohol compounds such as ethylene glycol, propylene glycol, butylene glycol, glycerin, trimethylolpropane, and pentaerythritol, and 9,9-bis[4-(2-hydroxyethoxy)phenyl]fluorene.

Examples of the acid dianhydride include tetracarboxylic acid dianhydrides exemplified in the description of the polyimide precursor.

Examples of the polysiloxane include a hydrolysis condensate using at least one organosilane compound. Examples of the organosilane compounds include tetrafunctional silanes such as tetramethoxysilane, tetraethoxysilane, tetraacetoxysilane, and tetraphenoxysilane; trifunctional silanes such as methyltrimethoxysilane, methyltriethoxysilane, methyltriisopropoxysilane, methyltri-n-butoxysilane, ethyltrimethoxysilane, ethyltriethoxysilane, ethyltriisopropoxysilane, ethyltri-n-butoxysilane, n-propyltrimethoxysilane, n-propyltriethoxysilane, n-butyltrimethoxysilane, n-butyltriethoxysilane, n-hexyltrimethoxysilane, n-hexyltriethoxysilane, decyltrimethoxysilane, vinyltrimethoxysilane, vinyltriethoxysilane, 3-methacryloxypropyltrimethoxysilane, 3-methacryloxypropyltriethoxysilane, 3-acryloxypropyltrimethoxysilane, phenyltrimethoxysilane, phenyltriethoxysilane, p-hydroxyphenyltrimethoxysilane, 1-(p-hydroxyphenyl)ethyltrimethoxysilane, 2-(p-hydroxyphenyl)ethyltrimethoxysilane, 4-hydroxy-5-(p-hydroxyphenylcarbonyloxy)pentyltrimethoxysilane, trifluoromethyltrimethoxysilane, trifluoromethyltriethoxysilane, 3,3,3-trifluoropropyltrimethoxysilane, 3-aminopropyltrimethoxysilane, 3-aminopropyltriethoxysilane, 3-glycidoxypropyltrimethoxysilane, 3-glycidoxypropyltriethoxysilane, 2-(3,4-epoxycyclohexyl)ethyltrimethoxysilane, 2-(3,4-epoxycyclohexyl)ethyltriethoxysilane, [(3-ethyl-3-oxetanyl)methoxy]propyltrimethoxysilane, [(3-ethyl-3-oxetanyl)methoxy]propyltriethoxysilane, 3-mercaptopropyltrimethoxysilane, 3-trimethoxysilylpropyl succinic acid, 1-naphthyltrimethoxysilane, 1-naphthyltriethoxysilane, 1-naphthyltri-n-propoxysilane, 2-naphthyltrimethoxysilane, 1-anthracenyltrimethoxysilane, 9-anthracenyltrimethoxysilane, 9-phenanthrenyltrimethoxysilane, 9-fluorenyltrimethoxysilane, 2-fluorenyltrimethoxysilane, 1-pyrenyltrimethoxysilane, 2-indenyltrimethoxysilane, and 5-acenaphthenyltrimethoxysilane; bifunctional silanes such as dimethyldimethoxysilane, dimethyldiethoxysilane, dimethyldiacetoxysilane, di-n-butyldimethoxysilane, diphenyldimethoxysilane, (3-glycidoxypropyl)methyldimethoxysilane, (3-glycidoxypropyl)methyldiethoxysilane, di(1-naphthyl)dimethoxysilane, and di(1-naphthyl) diethoxysilane; and monofunctional silanes such as trimethylmethoxysilane, tri-n-butylethoxysilane, (3-glycidoxypropyl)dimethylmethoxysilane, and (3-glycidoxypropyl)dimethylethoxysilane. Two or more of these organosilanes may be used.

Hydrolysis reaction conditions of the organosilane compounds may be appropriately set, and for example, it is preferable that an acid catalyst and water are added to the organosilane compounds over 1 to 180 minutes in a solvent, and then the mixture is reacted at room temperature to 110° C. for 1 to 180 minutes. When the hydrolysis reaction is performed in such conditions, a rapid reaction can be suppressed. A reaction temperature is more preferably 30 to 105° C.

Further, the hydrolysis reaction is preferably performed in the presence of the acid catalyst. As the acid catalyst, an acidic aqueous solution containing formic acid, acetic acid or phosphoric acid is preferred. The content of these acid catalyst is preferably 0.1 to 5 parts by mass based on 100 parts by mass of all the organosilane compounds used in the hydrolysis reaction. When the content of the acid catalyst is in this range, the hydrolysis reaction can be easily controlled to proceed to a necessary and sufficient extent.

With respect to conditions of the condensation reaction, for example, it is preferred that after a silanol compound is obtained by the hydrolysis reaction of the organosilane compounds, a reaction liquid is heated for 1 to 100 hours at a temperature of 50° C. to a boiling point of the solvent or lower as it is. Further, it is also possible to reheat the reaction liquid or add a base catalyst to the reaction liquid in order to increase a degree of polymerization of the polysiloxane. Further, after the hydrolysis reaction, an appropriate amount of the produced alcohol and the like may be distilled off and removed by heating and/or reduced pressure, and then an arbitrary solvent may be added as necessary.

Examples of the acrylic resin include a resin obtained by radically polymerizing a (meth)acrylic acid or a (meth) acrylic acid ester is preferable. Among them, a carboxyl group-containing acrylic resin is preferable from a viewpoint of patternability, and it is preferable that an ethylenically unsaturated double bond group is introduced into at least a part of the carboxyl group-containing acrylic resin from a viewpoint of cured film hardness.

Examples of the method for synthesizing the acrylic resin include radical polymerization of a (meth)acrylic compound. Examples of the (meth)acrylic compound include a carboxyl group-containing and/or acid anhydride group-containing (meth)acrylic compound and other (meth)acrylic acid esters. As the catalyst for the radical polymerization, for example, azo compounds such as azobisisobutyronitrile or organic peroxides such as benzoyl peroxide are commonly used.

The conditions of the radical polymerization may be appropriately set, but it is preferable that a carboxyl group-containing and/or an acid anhydride group-containing (meth)acrylic compound, and (meth)acrylic acid ester and a radical polymerization catalyst are added in a solvent, the inside of the reaction vessel is sufficiently replaced with nitrogen by bubbling, vacuum degassing, or the like, and then the reaction is performed at 60 to 110° C. for 30 to 300 minutes. When an acid anhydride group-containing (meth) acrylic compound is used, it is preferable to add a theoretical amount of water and react the mixture at 30 to 60° C. for 30 to 60 minutes. Further, a chain transfer agent such as a thiol compound may be used as necessary.

Examples of the (meth)acrylic acid ester include methyl (meth)acrylate, ethyl(meth)acrylate, propyl(meth)acrylate, cyclopropyl(meth)acrylate, cyclopentyl(meth)acrylate, cyclohexyl(meth)acrylate, cyclohexenyl(meth)acrylate, 4-methoxycyclohexyl(meth)acrylate, 2-cyclopropyloxycarbonylethyl(meth)acrylate, 2-cyclopentyloxycarbonylethyl (meth)acrylate, 2-cyclohexyloxycarbonylethyl(meth)acrylate, 2-cyclohexenyloxycarbonylethyl(meth)acrylate, 2-(4-methoxycyclohexyl)oxycarbonylethyl(meth)acrylate, norbornyl(meth)acrylate, isobornyl(meth)acrylate, tetracyclodecanyl(meth)acrylate, dicyclopentenyl(meth)acrylate, adamantyl(meth)acrylate, 2-methyladamantyl(meth)acrylate, and 1-methyladamantyl(meth)acrylate.

Further, the acrylic resin may be a copolymer of a (meth)acrylic compound and another unsaturated double bond-containing monomer. Examples of other unsaturated double bond-containing monomers include styrene, p-methylstyrene, o-methylstyrene, m-methylstyrene, α-methylstyrene, p-hydroxystyrene, maleic anhydride, norbornene, norbornene dicarboxylic acid, norbornene dicarboxylic anhydride, cyclohexene, butyl vinyl ether, butyl allyl ether, 2-hydroxyethyl vinyl ether, 2-hydroxyethyl allyl ether, cyclohexane vinyl ether, cyclohexane allyl ether, and 4-hydroxybutyl vinyl ether.

As the acrylic resin having an ethylenically unsaturated bond, those obtained by radically polymerizing a carboxyl group-containing and/or an acid anhydride group-containing (meth)acrylic compound, (meth)acrylic acid ester and/or another unsaturated double bond-containing monomer, and then performing an addition reaction with an epoxy compound having an ethylenically unsaturated double bond group are preferable. Examples of the catalyst used in the addition reaction include amino catalysts such as dimethylaniline, 2,4,6-tris(dimethylaminomethyl)phenol, and dimethylbenzylamine, phosphorus catalysts such as triphenylphosphine, ammonium catalysts such as tetrabutylammonium acetate, and chromium catalysts such as chromium acetylacetonate and chromium chloride.

Examples of the epoxy compound having an ethylenically unsaturated double bond group include glycidyl(meth)acrylate, α-ethylglycidyl(meth)acrylate, α-n-propylglycidyl (meth)acrylate, α-n-butylglycidyl(meth)acrylate, 3,4-epoxybutyl(meth)acrylate, 3,4-epoxyheptyl(meth)acrylate, α-ethyl-6,7-epoxyheptyl(meth)acrylate, butyl vinyl ether, butyl allyl ether, 2-hydroxyethyl vinyl ether, 2-hydroxyethyl allyl ether, cyclohexane vinyl ether, cyclohexane allyl ether, 4-hydroxybutyl vinyl ether, 4-hydroxybutyl allyl ether, allyl glycidyl ether, vinyl glycidyl ether, o-vinylbenzyl glycidyl ether, m-vinylbenzyl glycidyl ether, p-vinylbenzyl glycidyl ether, α-methyl-o-vinylbenzyl glycidyl ether, α-methyl-m-vinylbenzyl glycidyl ether, α-methyl-p-vinylbenzyl glycidyl ether, 2,3-diglycidyloxymethylstyrene, 2,4-diglycidyloxymethylstyrene, 2,5-diglycidyloxymethylstyrene, 2,6-diglycidyloxymethylstyrene, 2,3,4-triglycidyloxymethylstyrene, 2,3,5-triglycidyloxymethylstyrene, 2,3,6-triglycidyloxymethylstyrene, 3,4,5-triglycidyloxymethylstyrene, and 2,4,6-triglycidyloxymethylstyrene.

Examples of the phenolic resin include a novolac resin and a resol resin, and the phenolic resin is obtained by polycondensation of various phenols alone or a mixture thereof with aldehydes such as formalin.

Examples of the phenols constituting a novolac resin and a resol phenol resin include phenol, p-cresol, m-cresol, o-cresol, 2,3-dimethylphenol, 2,4-dimethylphenol, 2,5-dimethylphenol, 2,6-dimethylphenol, 3,4-dimethylphenol, 3,5-dimethylphenol, 2,3,4-trimethylphenol, 2,3,5-trimethylphenol, 3,4,5-trimethylphenol, 2,4,5-trimethylphenol, methylenebisphenol, methylenebis p-cresol, resorcin, catechol, 2-methylresorcin, 4-methylresorcin, o-chlorophenol, m-chlorophenol, p-chlorophenol, 2,3-dichlorophenol, m-methoxyphenol, p-methoxyphenol, p-butoxyphenol, o-ethylphenol, m-ethylphenol, p-ethylphenol, 2,3-diethylphenol, 2,5-diethylphenol, p-isopropylphenol, α-naphthol, and B-naphthol, and these can be used alone or as a mixture thereof.

Further, examples of the aldehydes used for polycondensation with the novolac resin or the resol resin include, in addition to formalin, paraformaldehyde, acetaldehyde, benzaldehyde, hydroxybenzaldehyde, and chloroacetaldehyde, and these can be used alone or as a mixture thereof.

Further, the phenol resin may have a structure in which some of hydrogen atoms added to the aromatic ring are substituted with one or more of an alkyl group having 1 to 20 carbon atoms, a fluoroalkyl group, a hydroxyl group, an alkoxyl group, an alkoxymethyl group, a methylol group, a carboxyl group, an ester group, a nitro group, a cyano group, a fluorine atom, and a chlorine atom.

In particular, from a viewpoint of dielectric reduction, a novolak resin or a resol resin having a rigid naphthalene structure or a biphenyl structure is more preferable, and specifically, p-phenylphenol, α-naphthol, or B-naphthol is preferably used as phenol. Further, examples of commercially available phenol resins include PN-80, PN-100, GPH-65, GPH-103 (the above are trade names, manufactured by Nippon Kayaku Co., Ltd.), XLC-3L (which is a trade name, manufactured by Mitsui Chemicals, Inc.), and MEHC-7851SS (which is a trade name, manufactured by Meiwa Plastic Industries, Ltd.), and GPH-65, GPH-103, and MEHC-7851SS having a rigid structure are particularly preferable.

The benzocyclobutene resin is produced, for example, by reacting a brominated arylcyclobutene compound with a compound containing an unsaturated alkyl group in the presence of a palladium catalyst. Specific examples thereof include divinylsiloxane bisbenzocyclobutene. Further, examples of the commercially available benzocyclobutene compound include CYCLOTENE 3022-63 or 4026-46 (the above are trade names, manufactured by The Dow Chemical Company).

The maleic acid resin is produced by, for example, copolymerizing maleic anhydride or maleic acid ester with a compound containing an unsaturated alkyl group under a radical polymerization catalyst. Specific examples thereof include a styrene maleic anhydride copolymer and maleic anhydride-modified polyethylene. Further, examples of commercially available maleic acid resins include XIRAN 1000, XIRAN 1440, XIRAN 2000, XIRAN 2500, XIRAN 3000, XIRAN 3500, XIRAN 4000, XIRAN 6000, and XIRAN 9000 (The above are trade names, manufactured by TOMOE Engineering Co., Ltd.).

The cycloolefin polymer is produced, for example, by hydrogenation ring-opening metathesis polymerization of norbornene, or by addition polymerization of norbornene and an unsaturated alkyl group-containing compound under a radical polymerization catalyst, followed by hydrogenation, or the like. Examples of the commercially available product include APL series (which is a trade name, Mitsui Chemicals, Inc.).

The content of the component (B) in the resin composition is preferably 10 parts by mass or more for forming a coating film having a film thickness of 1 μm or more with respect to 100 parts by mass of the component (A), and is preferably 500 parts by mass or less for sufficiently reducing the dissipation factor of the obtained cured film.

The photosensitive resin composition of the present invention contains the component (C). By containing the component (C), the active species that starts the crosslinking reaction of the component (A) is generated during exposure, and the pattern workability becomes possible through a subsequent development step. The component (C) is not particularly limited as long as it is a compound that generates a radical by exposure, but an alkylphenone compound, an aminobenzophenone compound, a diketone compound, a ketoester compound, a phosphine oxide compound, an oxime ester compound, and a benzoic acid ester compound are preferable because they are excellent in sensitivity, stability, and ease of synthesis. Among them, from a viewpoint of sensitivity, an alkylphenone compound and an oxime ester compound are preferable, and an oxime ester compound is particularly preferable. Further, in a case of a thick film having a processed film thickness of 5 μm or more, a phosphine oxide compound is preferable from a viewpoint of resolution.

As the alkylphenone compound, a known alkylphenone compound can be contained. Examples thereof include a-aminoalkylphenone compounds such as 2-methyl-[4-(methylthio)phenyl]-2-morpholinopropane-1-one, 2-dimethylamino-2-(4-methylbenzyl)-1-(4-morpholine-4-yl-phenyl)-butane-1-one, or 2-benzyl-2-dimethylamino-1-(4-morpholinophenyl)-butanone-1; a-hydroxyalkylphenone compounds such as 2-hydroxy-2-methyl-1-phenylpropane-1-one; α-alkoxyalkylphenone compounds such as 4-benzoyl-4-methylphenyl ketone; and acetophenone compounds such as p-t-butyldichloroacetophenone.

Among them, α-aminoalkylphenone compounds such as 2-methyl-[4-(methylthio)phenyl]-2-morpholinopropane-1-one, 2-dimethylamino-2-(4-methylbenzyl)-1-(4-morpholine-4-yl-phenyl)-butane-1-one, or 2-benzyl-2-dimethylamino-1-(4-morpholinophenyl)-butanone-1 are preferable because of their high sensitivity.

As the phosphine oxide compound, a known phosphine oxide compound can be contained. Examples thereof include 6-trimethylbenzoylphenylphosphine oxide, bis(2,4,6-trimethylbenzoyl)-phenylphosphine oxide, and bis(2,6-dimethoxybenzoyl)-(2,4,4-trimethylpentyl)-phosphine oxide.

Examples of the oxime ester compound include 1-phenyl-1,2-propanedione-2-(o-ethoxycarbonyl)oxime, 1-[9-ethyl-6-(2-methylbenzoyl)-9H-carbazole-3-yl]-,1-(0-acetyloxime), NCI-831, NCI-930 (the above are manufactured by ADEKA Corporation), and OXE-03, OXE-04 (the above are manufactured by BASF Japan Ltd.).

Among them, from a viewpoint of sensitivity, 1-[9-ethyl-6-(2-methylbenzoyl)-9H-carbazole-3-yl]-,1-(0-acetyloxime), 2-octanedione,1-[4-(phenylthio)-2-(0-benzoyloxime)], NCI-831, NCI-930, OXE-03, and OXE-04 are preferable.

As the aminobenzophenone compound, a known aminobenzophenone compound can be contained. Examples thereof include 4,4-bis(dimethylamino)benzophenone.

Examples of the diketone compound include a known compound such as benzyl.

Examples of the ketoester compound include a known compound such as methyl benzoylformate and ethyl benzoylformate.

Examples of the benzoic acid ester compound include a known compound such as methyl o-benzoylbenzoate, ethyl p-dimethylaminobenzoate, and 2-ethylhexyl-4-(dimethylamino)benzoate.

Other specific examples of the component (C) include a known one such as triphenylphosphine, carbon tetrabromide, and tribromophenylsulfone.

When a sum of the components (A) and (B) is 100 parts by mass, the content of the component (C) is preferably 0.5 parts by mass or more and 20 parts by mass or less because a sufficient sensitivity can be obtained and the amount of degassing during thermal curing can be suppressed. Among them, the content is more preferably 1.0 parts by mass or more and 10 parts by mass or less.

A sensitizer may be included for a purpose of enhancing the function of the component (C). By containing the sensitizer, the sensitivity can be improved and a photosensitive wavelength can be adjusted. As the sensitizer, a known sensitizer can be contained. Examples of the sensitizer include, but are not limited to, bis(dimethylamino)benzophenone, bis(diethylamino)benzophenone, diethylthioxanthone, N-phenyldiethanolamine, N-phenylglycine, 7-diethylamino-3-benzoylcoumarin, 7-diethylamino-4-methylcoumarin, N-phenylmorpholine, and derivatives thereof.

The photosensitive resin composition of the present invention preferably further contains a crosslinking agent (D) (hereinafter, may be omitted as a "component (D)"). The component (D) is a compound having a functional group crosslinked by heat, and specific examples of the functional group include an epoxy group, an oxetane group, and a methylol group.

The component (D) preferably contains one or more substance selected from the group consisting of an epoxy compound, an oxetane compound, and a methylol compound, and more preferably contains a methylol compound from a viewpoint of reducing the dielectric constant and the dielectric loss tangent.

As the epoxy compound, a known epoxy compound can be contained. Preferred examples of the epoxy compound include Epolite (registered trademark) 40E, Epolite 100E, Epolite 200E, Epolite 400E, Epolite 70P, Epolite 200P, Epolite 400P, Epolite 1500NP, Epolite 80MF, Epolite 4000, and Epolite 3002 (the above are trade names, manufactured by KYOEISHA CHEMICAL Co., LTD.), Denacol EX-212L, Denacol EX-214L, Denacol EX-216L, Denacol EX-321L, and Denacol EX-850L (the above are trade names, manufactured by Nagase ChemteX Corporation), Epikote 828, Epikote 1002, Epikote 1750, Epikote 1007, YX8100-BH30, E1256, E4250, and E4275 (the above are trade names, manufactured by Japan Epoxy Resin Co., Ltd.), EPICLON EXA-9583, EPICLON N695, HP4032, and HP7200 (the above are trade names, manufactured by DIC CORPORATION), VG3101 (which is a trade name, manufactured by Mitsui Chemicals, Inc.), TEPIC S, TEPIC G, and TEPIC P (the above are trade names, manufactured by Nissan Chemical Corporation), EPOTOHTO YH-434L (which is a trade name, manufactured by Tohto Kasei Co., Ltd.), and GAN, GOT, EPPN502H, NC3000, or NC6000 (the above are trade names, manufactured by Nippon Kayaku Co., Ltd.).

As the oxetane compound, a known oxetane compound can be contained. Examples thereof include OXT-101, OXT-121, OXT-212, and OXT-221 (the above are trade names, manufactured by TOAGOSEI CO., LTD.), ETERNACOLL EHO, ETERNACOLL OXBP, ETERNACOLL OXTP, ETERNACOLL OXMA, ETERNACOLL OXIPA (the above are trade names, manufactured by UBE Corporation), and oxetanized phenol novolac.

As the methylol compound, a known methylol compound can be contained. Preferable examples of the compound include DML-PC, DML-PEP, DML-OC, DML-OEP, DML-34X, DML-PTBP, DML-PCHP, DML-OCHP, DML-PFP, DML-PSBP, DML-POP, DML-MBOC, DML-MBPC, DML-MTrisPC, DML-BisOC-Z, DMLBisOCHP-Z, DML-BPC, DML-BisOC-P, DMOM-PC, DMOM-PTBP, DMOM-MBPC, TriML-P, TriML-35XL, TML-HQ, TML-BP, TML-pp-BPF, TML-BPE, TML-BPA, TML-BPAF, TML-BPAP, TMOM-BP, TMOM-BPE, TMOM-BPA, TMOM-BPAF, TMOM-BPAP, HML-TPPHBA, HML-TPHAP, HMOM-TPPHBA, and HMOM-TPHAP (the above are trade names, manufactured by Honshu Chemical Industry Co., Ltd.), NIKALAC (registered trademark) MX-290, NIKALAC MX-280, NIKALAC MX-270, NIKALAC MX-279, NIKALAC MW-100LM, and NIKALAC MX-750LM (the above are trade names, manufactured by SANWA Chemical Co., Ltd.).

When a total amount of the component (A) is 100 parts by mass, the content of the component (D) is preferably 5 parts by mass or more and 100 parts by mass or less, and more preferably 10 parts by mass or more and 90 parts by mass or less, from a viewpoint of obtaining high chemical resistance of the cured film and reducing the dielectric constant and the dielectric loss tangent.

The photosensitive resin composition may contain a solvent. Examples of the solvent include polar aprotic solvents such as N-methyl-2-pyrrolidone, y-butyrolactone, y-valerolactone, 5-valerolactone, N,N-dimethylformamide, N,N-dimethylacetamide, dimethylsulfoxide, 1,3-dimethyl-2-imidazolidinone, N,N'-dimethylpropyleneurea, N,N-dimethylisobutyramide, and methoxy-N,N-dimethylpropionamide; ethers such as tetrahydrofuran, dioxane, propylene glycol monomethyl ether, and propylene glycol monoethyl ether; ketones such as acetone, methyl ethyl ketone, and diisobutyl ketone; esters such as ethyl acetate, butyl acetate, isobutyl acetate, propyl acetate, propylene glycol monomethyl ether acetate, and 3-methyl-3-methoxybutyl acetate; alcohols such as ethyl lactate, methyl lactate, diacetone alcohol, and 3-methyl-3-methoxybutanol; and aromatic hydrocarbons, such as toluene and xylene. Two or more of these solvents may be contained.

The content of the solvent is preferably 100 parts by mass or more based on 100 parts by mass of the component (A) in order to dissolve the composition, and preferably 1,500 parts by mass or less in order to form a coating film having a thickness of 1 μm or more.

The photosensitive resin composition may contain a known antioxidant, surfactant, and adhesion improver.

The cured film of the present invention is a cured film obtained by curing the photosensitive resin composition of the present invention.

The cured film is obtained by applying the photosensitive resin composition to a substrate and drying the photosensitive resin composition for solvent volatilization. Thereafter, an exposure step and a post-exposure baking step are performed as necessary, and then a temperature of 150° C. to 350° C. is added for curing. This heat treatment is performed for five minutes to five hours while selecting a certain temperature and gradually raising the temperature or selecting a certain temperature range and continuously raising the temperature. As an example, the heat treatment is performed at 130° C. and 200° C. for 30 minutes each. A lower limit of the curing conditions in the present invention is preferably 170° C. or higher, but more preferably 180° C. or higher for proceeding curing sufficiently. Further, an upper limit of the curing conditions is not particularly limited, but is preferably 280° C. or lower, more preferably 250° C. or lower, still more preferably 230° C. or lower from a viewpoint of suppressing film shrinkage and stress.

When the cured film is subjected to pattern workability, the resin composition may be subjected to pattern workability by a known method including a coating step, a drying step, an exposure step, a development step, a post-exposure baking step, a thermal curing step, and the like.

The electronic component of the present invention has the cured film of the present invention.

The cured film formed from the photosensitive resin composition of the present invention can be used as an insulation film and a protective film constituting the electronic component.

Specific examples of the electronic component include active components having a semiconductor such as transistors, diodes, integrated circuits (ICs), and memories, as well as passive components such as resistors, capacitors, and inductors. Further, an electronic component using a semiconductor is also referred to as a semiconductor device or a semiconductor package.

Specific examples of the cured film in the electronic component are suitably used for uses such as a passivation film of a semiconductor, a semiconductor element, a surface protective film such as a thin film transistor (TFT), an interlayer insulating film such as an interlayer insulating film between rewirings in a multilayer wiring for high-density mounting of 2 to 10 layers, an insulation film of a touch panel display, a protective film, and an insulating layer of an organic electroluminescent element, but are not limited thereto, and can have various structures.

Further, a substrate surface on which the cured film is formed can be appropriately selected depending on the uses and steps, and examples thereof include silicon, ceramics, glass, metal, and epoxy resin, and a plurality of these may be disposed in the same plane.

An antenna element using the cured film of the present invention will be described. The antenna element of the present invention is an antenna element including at least one or more antenna wires and the cured film of the present invention, in which the antenna wires include any one or more selected from the group consisting of a meander-shaped loop antenna, a coil-shaped loop antenna, a meander-shaped monopole antenna, a meander-shaped dipole antenna, or a planar antenna, the antenna wires have an occupied area of 1000 $mm^2$ or less per antenna unit, and the cured film is an insulation film that insulates the ground from the antenna wires.

FIG. 1 is a schematic view of a coplanar feeding type microstrip antenna that is a type of planar antenna. FIG. 1*a* illustrates a cross-sectional view, and FIG. 1*b* illustrates a top view. To start with, a forming method will be described. The photosensitive resin composition according to the present invention is applied onto a copper foil, prebaked, and exposed, and then the copper foil is laminated and thermally cured to form a cured film having the copper foil on both sides. Thereafter, the antenna element having an antenna pattern of copper wiring of the microstrip line (MSL) illustrated in FIG. 1 is obtained through patterning by a subtract method.

Next, the antenna pattern of FIG. 1 will be described. In FIG. 1*a*, a reference numeral 15 denotes the ground (the entire surface), and a reference numeral 16 denotes an insulation film serving as a substrate of the antenna. Upper layers 11 to 13 thereof indicate cross sections of the antenna wiring obtained by the patterning. A ground wiring thickness J and an antenna wiring thickness K can have any thickness depending on an impedance design, but are generally 2 to 20 μm. In FIG. 1*b*, a reference numeral 11 denotes an antenna unit, a reference numeral 12 denotes a matching circuit, a reference numeral 13 denotes an MSL feeding line, and a reference numeral 14 denotes a feeding point. In order to match the impedance of the antenna unit 11 and the feeding line 13, a length M of the matching circuit 12 has a length of ¼ λr (λr=(wavelength of transmission radio wave)/(dielectric constant of insulating material) ½). Further, a width W and a length L of the antenna unit 11 are designed to be ½ λr. The antenna unit length L may be ½ λr or less according to the design of the impedance. Since the cured film of the present invention has a low dielectric constant and a low dissipation factor, it is possible to provide an antenna element with high efficiency and high gain. Further, from these characteristics, the antenna element using the insulation film of the present invention is suitable as an antenna for high frequency, and a small antenna element can be formed by setting an area (=L×W) of the antenna unit to a size of 1000 $mm^2$ or less. In this way, a high-frequency antenna element having high efficiency, high gain, and small size is obtained.

Next, a semiconductor package including a semiconductor element such as an IC chip, a rewiring layer, a sealing resin, and an antenna wiring will be described. A semiconductor package of the present invention is a semiconductor package including at least a semiconductor element, a rewiring layer, a sealing resin, and an antenna wiring, in which the antenna wiring includes at least one or more selected from the group consisting of a meander-shaped loop antenna, a coil-shaped loop antenna, a meander-shaped monopole antenna, a meander-shaped dipole antenna, and a microstrip antenna, an occupied area of the antenna wiring per antenna unit is 1000 $mm^2$ or less, an insulating layer of the rewiring layer and/or the sealing resin include the cured film of the present invention, and the sealing resin is between a ground and the antenna wiring.

Figure 2:
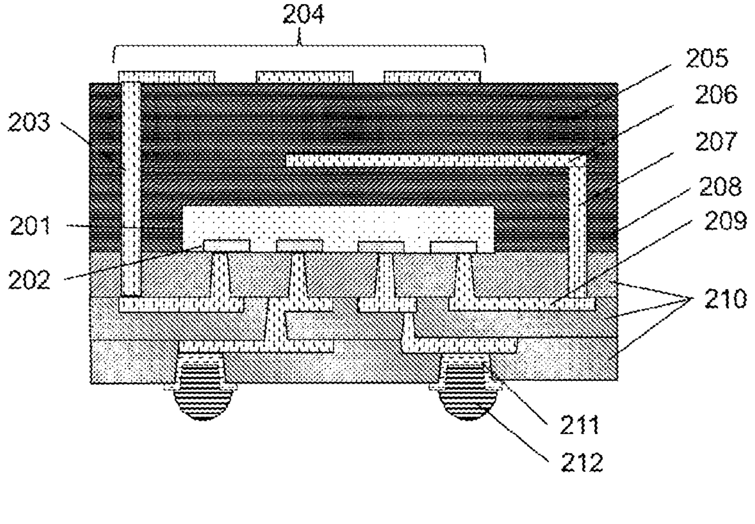
FIG. 2 is a schematic view of a cross section of a semiconductor package.

FIG. 2 is a schematic view of a cross section of a semiconductor package including an IC chip (a semiconductor element), rewiring, a sealing resin, and an antenna element. On an electrode pad 202 of an IC chip 201, a rewiring layer (with two layers of copper and three layers of insulation film) is formed by a copper wiring 209 and an insulation film 210 formed by the cured film of the present invention. A barrier metal 211 and a solder bump 212 are formed on a pad of the rewiring layer (the copper wiring 209 and the insulation film 210). In order to seal the IC chip, a first sealing resin 208 made of the cured film of the present invention is formed, and the copper wiring 209 serving as a ground for an antenna is further formed thereon. A first via wiring 207 that connects a ground 206 and the rewiring layer (the copper wiring 209 and the insulation film 210) is formed via a via hole formed in the first sealing resin 208. A second sealing resin 205 made of the cured film of the present invention is formed on the first sealing resin 208 and a ground wiring 206, and a planar antenna wiring 204 is formed thereon. A second via wiring 203 that connects the planar antenna wiring 204 and the rewiring layer (the copper wiring 209 and the insulation film 210) is formed via a via hole formed in the first sealing resin 208 and second sealing resin 205. A thickness per layer of the insulation film 210 is preferably 10 to 20 μm, and the first sealing resin and the second sealing resin are preferably 50 to 200 μm and 100 to 400 μm, respectively. Since the cured film of the present invention has a low dielectric constant and a low dissipation factor, a semiconductor package including an antenna element to be obtained has high efficiency and high gain, and the transmission loss in the package is small.

In other words, it is preferable that the electronic component of the present invention is an electronic component including at least one antenna wiring and an antenna element including the cured film of the present invention, in which the antenna wiring includes any one or more selected from the group consisting of a meander-shaped loop antenna, a coil-shaped loop antenna, a meander-shaped monopole antenna, a meander-shaped dipole antenna, or a planar antenna, the antenna wiring has an occupied area of 1000 $mm^2$ or less per antenna unit, and the cured film is an insulation film that insulates the ground from the antenna wiring.

Furthermore, it is preferable that the electronic component of the present invention is an electronic component including a semiconductor package having at least a semiconductor element, a rewiring layer, a sealing resin, and an antenna wiring, and the insulating layer of the rewiring layer and/or the sealing resin include the cured film of the present invention, and the sealing resin also has a function as an insulation film that insulates between the ground and the antenna wiring.

Furthermore, it is preferable that the electronic component of the present invention is an electronic component including an antenna wiring and an antenna element obtained by laminating the cured film of the present invention, and the height of the antenna wiring is 50 to 200 μm, and the thickness of the cured film is 80 to 300 μm. By laminating the antenna wiring and the cured film and setting the height of the antenna wiring and the thickness of the cured film within the above ranges, transmission and reception can be performed in a small size and in a wide range, and since the cured film of the present invention has a low dielectric constant and a low dissipation factor, an antenna element with high efficiency and high gain can be provided.

Further, the compound of the present invention is a compound represented by expression (1) or a compound represented by expression (2).

[Chem. 18]

(1)

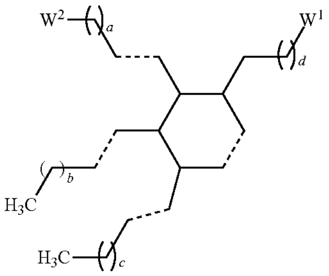

In expression (1), $W^1$ and $W^2$ each independently represent a group represented by expression (3) or expression (4). In expression (1), a, b, c, and d are natural numbers each independently satisfying a+b=6 to 17 and c+d=8 to 19, and the broken line part means a carbon-carbon single bond or a carbon-carbon double bond.

[Chem. 19]

(2)

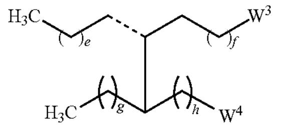

In expression (2), $W^3$ and $W^4$ each independently represent a group represented by expression (3) or expression (4). In expression (2), e, f, g, and h are each independently a natural number satisfying e+f=5 to 16 and g+h=8 to 19, and the broken line part means a carbon-carbon single bond or a carbon-carbon double bond.

[Chem. 20]

(3)

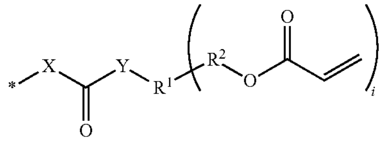

(4)

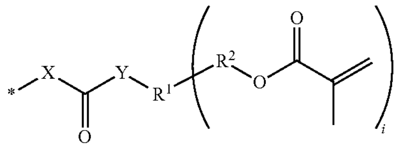

In expression (3) and expression (4), X and Y represent —NH—. $R^1$ represents a single bond or a 2 to 6 valent organic group having 1 to 5 carbon atoms. $R^2$ represents a single bond or a divalent organic group having 1 to 5 carbon atoms. i represents an integer 1 to 5. A sign of * indicates a point of bonding.

Since the compound of the present invention can be crosslinked by radical polymerization, it can be easily cured by being combined with a photo or thermal radical generator, and the cured film has a low dielectric constant and a low dissipation factor. Further, it has high solubility in an organic solvent and excellent compatibility with many resins. Therefore, low dielectric properties can be imparted to various resins. The reason why these characteristics are obtained is not clear, but it is presumed that these characteristics are obtained because a low-polarity site and a high-polarity site are combined in the molecule.

EXAMPLES

The present invention will be illustrated below with reference to Examples, but it should be understood that the present invention is not construed as being limited thereto. First, the evaluation method in each Example and Comparative Example will be described. For evaluation, a photosensitive resin composition before curing (hereinafter referred to a varnish) that was previously filtered through a polytetrafluoroethylene filter with an average diameter of 1 μm (manufactured by Sumitomo Electric Industries, Ltd.) was used.

(1) Patternability

The varnish was applied with a spin coater (1H-360S manufactured by Mikasa Co., Ltd.) to a silicon wafer by spin coating, and then the silicon wafer was prebaked at 100° C.

for 3 minutes using a hot plate (SCW-636 manufactured by Dainippon Screen Mfg. Co., Ltd.) to prepare a prebaked film having a film thickness of 11 μm. Using a parallel light mask aligner (hereinafter referred to as PLA) (PLA-501F manufactured by Canon Inc.), the obtained prebaked film was subjected to contact exposure at 500 mJ/cm$^2$ through a mask having a 30 μm 1:1 line and space pattern using an ultra-high pressure mercury lamp as a light source (g, h, i line mixing).

Thereafter, the post-exposure baking was performed at 120° C. for 1 minute, and development was performed using a coater and developer MARK-7. In a case of development with an organic solvent, puddle development was performed using an appropriate developer for a material to be evaluated, and then the silicon wafer was rinsed with an appropriate rinse solution in the same manner. The developer and the rinse solution used are shown in Table 4. Further, when the photosensitive resin composition was dissolved in an aqueous alkali solution, the photosensitive resin composition was developed with 2.38% by mass aqueous tetramethylammonium (TMAH) solution and then rinsed with pure water.

As for development time, for each prebaked film, development start time was set to 0 seconds in advance, time during which all of the prebaked film was eluted into the developer was measured between 0 seconds and 90 seconds, and when all of the prebaked film was eluted between 0 seconds and 90 seconds, twice the time was defined as the development time. On the other hand, when all of the prebaked film was not completely eluted within 90 seconds from the start of development, the development time was set to 3 minutes. Rinse time was all 30 seconds. After the development, a pattern workability portion was observed, and developability was evaluated by defining a case where no residue remained in a space portion in a 30 μm 1:1 line and space as A, a case where a residue was observed as B, and a case where the film was not dissolved in a developer and remained as C.

The film thickness was measured after development, and a residual film rate obtained by dividing the film thickness after development of an exposed portion by the prebaked film thickness when the prebaked film thickness was set to 100 was measured. When the residual film ratio was 80% or more, the sensitivity was evaluated as A, when the residual film ratio was 50% or more and less than 80%, the sensitivity was evaluated as B, and when the residual film ratio was less than 50%, the sensitivity was evaluated as C. In addition, the film thickness was measured under the condition of a refractive index of 1.629 using Lambda Ace S™-602 manufactured by Dainippon Screen Mfg. Co., Ltd. The same applies to the film thickness described below.

(2) Measurement of Dielectric Constant and Dielectric Loss Tangent

The varnish was applied onto a 6-inch silicon wafer by a spin coating method and prebaked using a coater and developer Mark-7 so that the film thickness after prebaking at 120° C. for 3 minutes was 11 μm, then the entire surface was exposed to 300 mJ/cm$^2$ using a PLA, the temperature was raised to 220° C. at 3.5° C./min at an oxygen concentration of 20 ppm or less using an inert oven CLH-21CD-S (manufactured by Koyo Thermo Systems Co., Ltd.), and heat treatment was performed at each temperature for 1 hour. When the temperature reached 50° C. or less, the silicon wafer was taken out and immersed in 45% by mass of hydrofluoric acid for 5 minutes to peel the cured film of the resin composition film off the wafer. This film was cut into a strip shape having a width of 3 cm and a length of 10 cm, and the dielectric constant and the dissipation factor at a frequency of 1 GHz were measured by a perturbation-type cavity resonator method in accordance with ASTMD2520 at a room temperature of 23.0° C. and a humidity of 45.0% RH. The dielectric properties were determined in five stages as shown in Table 1 below.

TABLE 1

Evaluation of dielectric properties (1 GHz)

| | Dielectric constant | | |
|---|---|---|---|
| Dissipation factor | Less than 3.0 | 3.0 or more and less than 3.5 | 3.5 or more |
| Less than 0.010 | A | B | C |
| 0.010 or more and less than 0.015 | B | C | D |
| 0.015 or more | C | D | E |

(3) Measurement of Glass Transition Point

A free standing film of a cured film was prepared in the same manner as in the "(2) Measurement of dielectric constant and dielectric loss tangent" described above, the cured film obtained by this method was cut out to a size of 3.0 cm×1.5 cm with a single blade, the temperature was raised from 25° C. to 400° C. at a rate of 10° C./min under a condition of 80 mL/min under a nitrogen flow using a thermomechanical analyzer (TMA/SS6100 manufactured by Seiko Instruments Inc.), and measurement was performed (measurement method (I)). Further, when the obtained cured film was not obtained as a free standing film, a cured film (a) was scraped off, the temperature was raised from 25° C. to 400° C. at a rate of 10° C./min in a nitrogen atmosphere using a differential scanning calorimeter (DSC-50 manufactured by Shimadzu Corporation), and measurement was performed (measurement method (II)). Evaluation criteria were as follows: the evaluation was performed in four stages. The higher the glass transition point is, the higher the heat resistance of the cured film is.

A: The glass transition point has a value of 200° C. or higher.

B: The glass transition point has a value of 170° C. or higher and lower than 200° C.

C: The glass transition point has a value of 140° C. or higher and lower than 170° C.

D: The glass transition point has a value of less than 140° C.

(4) Measurement of Elongation at Break of Cured Film after Curing

A free standing film of a cured film was prepared in the same manner as in the "(2) Measurement of dielectric constant and dielectric loss tangent" described above, the film was cut into a strip shape having a width of 1.5 cm and a length of 9 cm, and pulled at a tensile speed of 50 mm/min at a room temperature of 23.0° C. and a humidity of 45.0% RH (a chuck distance=2 cm) using Tensilon RTM-100 (manufactured by ORIENTEC CO., LTD), and the elongation at break (%) was measured. The measurement was performed on 10 strips per sample, and the average value of the top 5 measured values ranked in descending order was determined from the results.

Hereinafter, abbreviations of compounds used in the synthesis examples and the examples will be described.

Priamine 1075: dimer diamine compound (which is a trade name, manufactured by Croda Japan K.K.) (an average amine value: 205)

Karenz AOI: 2-Acryloyloxyethyl isocyanate (which is a trade name, manufactured by Showa Denko K.K.)

Karenz BEI: 1,1-(Bisacryloyloxymethyl)ethyl isocyanate (which is a trade name, manufactured by Showa Denko K.K.)

Polyflow 77: Acrylic surfactant (which is a trade name, manufactured by KYOEISHA CHEMICAL Co., LTD.)

TMAH: Tetramethylammonium aqueous solution

VG-3101: Monomer-type triphenylmethane-type epoxy resin (which is a trade name, manufactured by Printec Corporation)

U-847: Acrylic monomer with the following structure having a urethane group (which is a trade name, manufactured by Designer Molcules Inc.)

[Chem. 21]

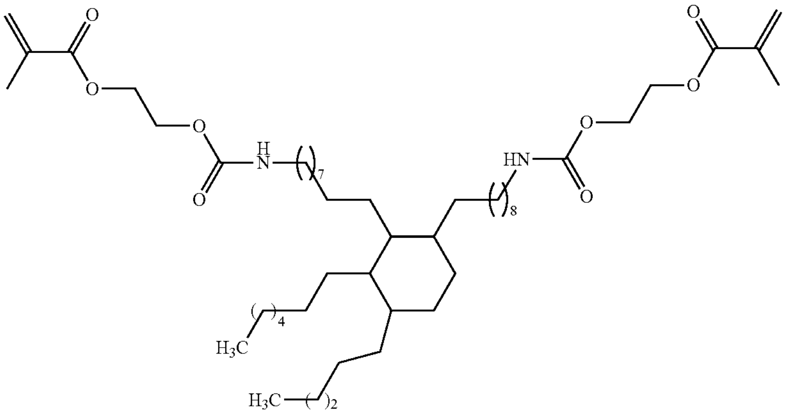

Methyl silicate 51: Silicate oligomer (which is a trade name, manufactured by COLCOAT CO., LTD.)

SiDA: 1,3-bis(3-aminopropyl)tetramethyldisiloxane

BAHF: 2,2-bis(3-amino-4-hydroxyphenyl)hexafluoropropane

BFE: 1,2-bis(4-formylphenyl)ethane

CP: Cyclopentanone

CYCLOTENE 4026-46: Benzocyclobutene solution (which is a trade name, manufactured by The Dow Chemical Company)

DCP-A: Dicyclopentadiene dimethacrylate (which is a trade name, manufactured by KYOEISHA CHEMICAL Co., LTD.)

DFA: Dimethylformamide dimethyl acetal

EL: Ethyl lactate

HEMA: 2-Hydroxyethyl methacrylate

HA: 2,2-bis[3-(3-aminobenzamide)-4-hydroxyphenyl]hexafluoropropane $H_2O$: Ultrapure water IPA: 2-Propanol IRGANOX 3114: Hindered phenol antioxidant (which is a trade name, manufactured by BASF Japan Ltd.)

GBL: γ-butyrolactone

KC cleaner NX: C10-12 of isoparaffin (which is a trade name, manufactured by Keiyo Chemical co., Ltd.)

MEHC-7851SS: Phenol resin (which is a trade name, manufactured by Meiwa Plastic Industries, Ltd.)

MOM: 4-[1,1-bis[4-hydroxy-3,5-bis(methoxymethyl)phenyl]ethyl]-2,6-bis(methoxymethyl)phenol NA: 5-Norbornene-2,3-dicarboxylic anhydride NCI-831: Photopolymerization initiator (which is a trade name, manufactured by ADEKA Corporation)

NMP: N-methyl-2-pyrrolidone

ODPA: 3,3',4,4'-Diphenylethertetracarboxylic acid dianhydride

OXT-121: Oxetane compound (a trade name, manufactured by TOAGOSEI CO., LTD.)

PGMEA: Propylene glycol methyl ether acetate

XIPAN 2000: Styrene maleic anhydride copolymer resin (which is a trade name, manufactured by TOMOE Engineering Co., Ltd.)

APL6015T: Cycloolefin polymer (which is a trade name, manufactured by Mitsui Chemicals, Inc.)

BMI-689: A monomer with the following structure having a maleimide group (which is a trade name, manufactured by Designer Molcules Inc.)

[Chem. 22]

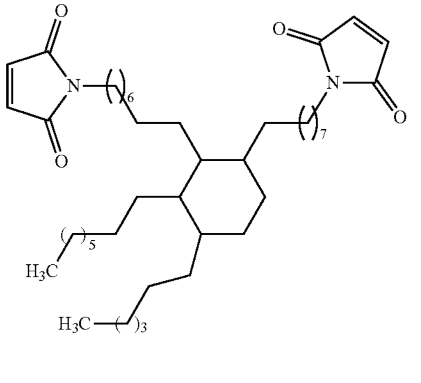

Example 1: Synthesis of Polyfunctional Monomer (M-1)

Under dry nitrogen flow, 28.22 g (0.20 mol) of Karenz AOI and 28.22 g of toluene were charged into a three-necked flask and stirred. Furthermore, a solution obtained by dissolving 53.50 g (0.10 mol) of the Priamine 1075 in 53.50 g of toluene was added dropwise. After completion of the dropwise addition, the mixture was stirred at room temperature for 12 hours, and then toluene was removed with an evaporator to obtain a polyfunctional monomer (M-1). The nuclear magnetic resonance apparatus (JNM-ECZ400R manufactured by JEOL Ltd.) was used to identify a structure of the obtained polyfunctional monomer. The results are shown below.

$^1$H-NMR (DMSO): 6.4 (d, 2H), 6.0-6.2 (m, 6H), 5.8 (d, 2H), 4.3 (m, 4H), 3.4 (m, 4H), 3.1 (m, 4H), 1.2-1.5 (m, 60H), 0.9 (t, 6H).

[Chem. 23]

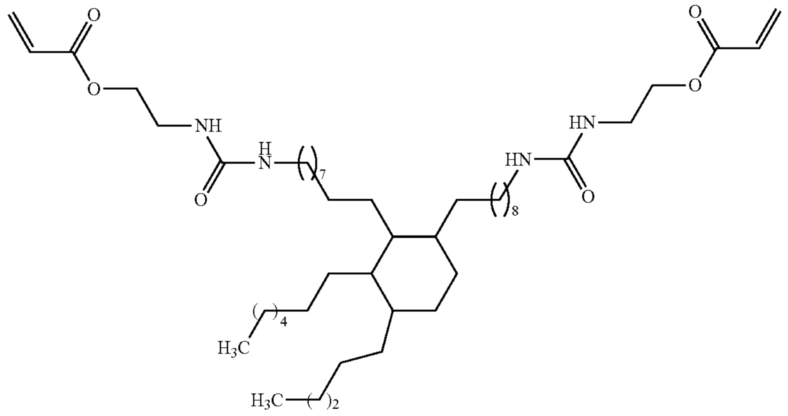

Example 2: Synthesis of Polyfunctional Monomer (M-2)

The same operation as in Synthesis Example 1 was carried out except that 28.22 g (0.20 mol) of Karenz AOI of Synthesis Example 1 was changed to 47.84 g (0.20 mol) of Karenz BEI to obtain a polyfunctional monomer (M-2). The results of NMR used for identification of the structure of the obtained polyfunctional monomer are shown below.

$^1$H-NMR (DMSO): 6.4-6.6 (m, 6H), 6.0-6.2 (m, 6H), 5.8 (d, 4H), 4.8 (s, 8H), 3.1 (m, 4H), 1.6 (s, 6H), 1.2-1.5 (m, 60H), 0.9 (t, 6H).

[Chem. 24]

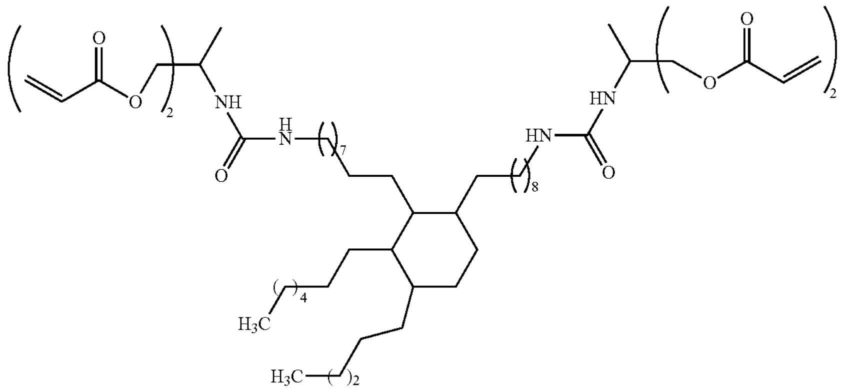

Synthesis Example 1: Synthesis of Polyimide (P-1)

Under dry nitrogen flow, 31.13 g (0.085 mol) of BAHF, 1.24 g (0.0050 mol) of SiDA, 2.18 g (0.020 mol) of MAP as an end-capping agent, and 150.00 g of NMP were weighed and dissolved in a three-necked flask. Into this, a solution in which 31.02 g (0.10 mol; 100 mol % relative to the structural unit derived from all of carboxylic acids and derivatives thereof) of ODPA was dissolved in 50.00 g of NMP was added. The resultant solution was stirred at 20° C. for one hour, and then further stirred at 50° C. for four hours. Thereafter, 15 g of xylene was added to the solution, and the resultant solution was stirred at 150° C. for five hours while azeotropically distilling water together with xylene. After completion of the reaction, the reaction solution was introduced into 3 L of water, and precipitated solid precipitates were collected by filtration. The obtained solid material was washed with water three times and was then dried with a vacuum dryer at 80° C. for 24 hours to produce a polyimide (P-1).

Synthesis Example 2: Synthesis of Polyamide (P-2)

In a 500 mL round-bottom flask equipped with a toluene-filled Dean-Stark water separator and a condenser tube, 19.98 g (0.095 mol; 95.0 mol % with respect to the structural units derived from all amines and derivatives thereof) of bis(4-aminocyclohexyl)methane, 1.24 g (0.0050 mol; 5.0 mol % with respect to the structural units derived from all amines and derivatives thereof) of SiDA, and 70.00 g of NMP were weighed and dissolved. Into this, a solution in which 19.06 g (0.080 mol; 66.7 mol % relative to the structural unit derived from all of carboxylic acids and derivatives thereof) of BFE was dissolved in 20.00 g of NMP was added. The resultant solution was stirred at 20° C. for one hour and then further stirred at 50° C. for two hours. Next, a solution prepared by dissolving 6.57 g (0.040 mol; 33.3 mol % relative to the structural unit derived from all of carboxylic acids and derivatives thereof) of NA was dissolved that served as an end-capping agent in 10 g of NMP was added to the solution, and the resultant solution was stirred at 50° C. for two hours. Thereafter, the solution was stirred at 100° C. for two hours under a nitrogen atmosphere. After completion of the reaction, the reaction solution was introduced into 3 L of water, and precipitated solid precipitates were collected by filtration. The obtained solid material was washed with water three times and was then dried with a vacuum dryer at 80° C. for 24 hours to produce a polyamide (P-2).

Synthesis Example 3: Synthesis of Polyurea (P-3)

Under dry nitrogen flow, 6.00 g (0.020 mol) of 4,4'-diphenylmethane diisocyanate was dissolved in 30 g of NMP, and the resultant solution was charged into a three-necked flask. While stirring the solution in the flask, a solution prepared by dissolving 3.52 g (0.013 mol) of 2-(3',5'-diaminobenzyloxy)ethyl methacrylate in 20 g of NMP was added to the solution, and the mixture was stirred at 50° C. for four hours. After completion of the reaction, the reaction solution was introduced into 500 g of methanol, and precipitated solid precipitates were collected by filtration. The obtained solid material was dried in a vacuum dryer for 24 hours to obtain polyurea (P-3).

Synthesis Example 4: Synthesis of Polyester Resin Solution (P-4)

148 g of 1,1-bis(4-(2,3-epoxypropyloxy)phenyl)-3-phenylindan, 47 g of acrylic acid, 1 g of tetrabutylammonium acetate (hereinafter, abbreviated as "TBAA"), 2.0 g of tert-butylcatechol and 244 g of PGMEA were charged, and the resulting mixture was stirred at 120° C. for five hours. After the mixture was cooled to room temperature, 30 g of biphenyltetracarboxylic dianhydride and 1 g of TBAA were added, and the resulting mixture was stirred at 110° C. for three hours. After the mixture was cooled to room temperature, 15 g of tetrahydrophthalic anhydride was added, and the resulting mixture was stirred at 120° C. for five hours. After completion of the reaction, 500 g of PGMEA was added, the reaction solution was separated by extraction with a 1 N formic acid aqueous solution in order to remove an addition catalyst, and the separated reaction solution was dried with magnesium sulfate and condensed by a rotary evaporator so that a concentration of a solid content is 40 wt % to obtain a polyester resin (P-4).

Synthesis Example 5: Synthesis of Polysiloxane Solution (P-5)

Under a dry nitrogen flow, 54.48 g (0.40 mol) of methyltrimethoxysilane, 99.15 g (0.50 mol) of phenyltrimethoxysilane, 12.32 g (0.05 mol) of 2-(3,4-epoxycyclohexyl) ethyltrimethoxysilane, 5.88 g (corresponding to 0.05 moles of Si atoms) of methyl silicate 51, and 155.04 g of propylene glycol monomethyl ether acetate (hereinafter, it may be referred to as PGMEA) were charged in a 500 ml three-necked flask, and an aqueous phosphoric acid solution obtained by dissolving 0.515 g (0.30 parts by mass with respect to the charged monomers) of phosphoric acid in 54.45 g of water was added over 10 minutes while stirring at room temperature. Thereafter, the flask was immersed in an oil bath at 40° C. and stirred for 60 minutes, and then the temperature of the oil bath was raised to 115° C. over 30 minutes. After one hour from start of temperature increase, an internal temperature of the solution reached 100° C., and then the solution was heated and stirred for two hours (the internal temperature was 100° C.) to obtain a polysiloxane solution (P-5).

Synthesis Example 6: Synthesis of Acrylic Resin Solution (P-6)

In a 500 ml flask, 3 g of 2,2'-azobis(isobutyronitrile) and 50 g of PGMEA were charged. Thereafter, 23.0 g of methacrylic acid, 31.5 g of benzyl methacrylate, and 32.8 g of tricyclo[5.2.1.0(2,6)]decane-8-yl methacrylate were charged thereinto, and stirred for a while at room temperature. The inside of the flask was thoroughly purged with nitrogen by bubbling, and the contents were heated and stirred at 70° C. for five hours. Next, 12.7 g of glycidyl methacrylate, 1 g of dimethylbenzylamine, 0.2 g of p-methoxyphenol, and 100 g of PGMEA were added to the obtained solution, and the mixture was heated and stirred at 90° C. for four hours. After stirring, PGMEA was added so that the concentration of solid content was 40 wt % to obtain an acrylic resin solution (P-6).

Synthesis Example 7: Synthesis of Polyimide Precursor (P-7)

Under a dry nitrogen flow, 31.02 g (0.10 mol) of ODPA was put in a 500 ml separable flask, and 26.03 g (0.20 mol) of HEMA and 123.0 ml of NMP were put therein. At room temperature, 22.26 g (0.22 mol) of triethylamine was added thereto with stirring to obtain a reaction mixture. After completion of heat generation due to the reaction, the reaction mixture was allowed to cool to room temperature and then allowed to stand for 16 hours. Next, the temperature was raised to 40° C., and 76.7 g (0.2 mol) of diphenyl (2,3-dihydro-2-thioxo-3-benzoxazolyl)phosphonate was added to the reaction mixture, then the mixture was stirred for 30 minutes. The mixture was further stirred at room temperature for two hours, then 17.88 g (0.085 mol; 77.3 mol % with respect to the structural units derived from all amines and derivatives thereof) of bis(4-aminocyclohexyl) methane, 1.24 g (0.0050 mol; 4.5 mol % with respect to structural units derived from all amines and derivatives thereof) of SiDA, 2.18 g (0.020 mol; 18.2 mol % with respect to structural units derived from all amines and derivatives thereof) of MAP as an end-capping agent, and 77.00 g of NMP were added, and the mixture was stirred for one hour to obtain a reaction solution. The obtained reaction solution was allowed to cool to room temperature, and added to 3 L of water to produce a precipitate composed of a crude polymer. This precipitate was collected by filtration, washed three times with water, then washed two times with 500 mL of isopropyl alcohol, and vacuum-dried to obtain a powdery polyimide precursor (P-7).

Synthesis Example 8: Synthesis of Polyimide Precursor (P-8)

The same operation as in Synthesis Example 5 was carried out except that 26.03 g (0.20 mol) of HEMA was changed to 53.70 g (0.20 mol) of oleyl alcohol to give a polyimide precursor (P-8).

Synthesis Example 9: Synthesis of Polyimide Precursor (P-9)

Under a dry nitrogen flow, 51.4 g (0.085 mol) of HA, 1.24 g (0.005 mol) of SiDA, and 2.18 g (0.020 mol) of MAP as an end-capping agent were dissolved in 200 g of NMP. To the obtained solution, 31.0 g (0.10 mol) of ODPA was added, and the resulting mixture was stirred at 40° C. for two hours. Thereafter, a solution prepared by diluting 7.14 g (0.06 mol) of DFA with 5 g of NMP was added dropwise over 10 minutes. After completion of the dropwise addition, stirring was continuously conducted at 40° C. for two hours. After completion of the stirring, the solution was put into 2 L of water, and the polymer solid precipitate was collected by filtration. Furthermore, the polymer solids were washed three times with 2 L of water, and the collected polymer solids were dried in a vacuum dryer at 50° C. for 72 hours to produce a polyimide precursor (P-9).

Synthesis Example 10: Synthesis of Polybenzoxazole (P-10)

34.79 g (0.095 mol; 95.0 mol % relative to the amount of structural units derived from all of amines and derivatives thereof) of BAHF, 1.24 g (0.0050 mol; 5.0 mol % relative to the amount of structural units derived from all of amines and derivatives thereof) of SiDA, and 75.00 g of NMP were weighed in a 500-mL round-bottom flask equipped with a Dean-Stark water separator and a condenser tube and having toluene filled therein, and then dissolved together. Into this, a solution in which 19.06 g (0.080 mol; 66.7 mol % relative to the structural unit derived from all of carboxylic acids and derivatives thereof) of BFE and 6.57 g (0.040 mol, 33.3 mol % relative to the structural unit derived from all of the carboxylic acids and derivatives thereof) of NA as an end-capping agent were dissolved in 25.00 g of NMP was added. Thereafter, stirring was performed at 20° C. for one hour and subsequently stirring was performed at 50° C. for one hour. Thereafter, under a nitrogen atmosphere, heating and stirring was performed at 200° C. or higher for 10 hours to conduct dehydration reaction. After completion of the reaction, the reaction solution was introduced into 3 L of water, and precipitated solid precipitates were collected by filtration. The obtained solid material was washed with water three times and dried by a vacuum dryer at 80° C. for 24 hours to obtain a polybenzoxazole (P-10).

Synthesis Example 11: Synthesis of Polybenzoxazole Precursor (P-11)

34.79 g (0.095 mol; 95.0 mol % relative to the amount of structural units derived from all of amines and derivatives thereof) of BAHF, 1.24 g (0.0050 mol; 5.0 mol % relative to the amount of structural units derived from all of amines and derivatives thereof) of SiDA, and 70.00 g of NMP were weighed in a 500 mL round-bottom flask equipped with a Dean-Stark water separator and a condenser tube and having toluene filled therein, and then dissolved together. Into this, a solution in which 19.06 g (0.080 mol; 66.7 mol % relative to the structural unit derived from all of carboxylic acids and derivatives thereof) of BFE was dissolved in 20.00 g of NMP was added. The resultant solution was stirred at 20° C. for one hour and then further stirred at 50° C. for two hours. Next, a solution prepared by dissolving 6.57 g (0.040 mol; 33.3 mol % relative to the structural unit derived from all of carboxylic acids and derivatives thereof) of NA was dissolved that served as an end-capping agent in 10 g of NMP was added to the solution, and the resultant solution was stirred at 50° C. for two hours. Thereafter, the solution was stirred at 100° C. for two hours under a nitrogen atmosphere. After completion of the reaction, the reaction solution was introduced into 3 L of water, and precipitated solid precipitates were collected by filtration. The obtained solid material was washed with water three times and then dried by a vacuum dryer at 80° C. for 24 hours to obtain a polybenzoxazole precursor (P-11).

Synthesis Example 12: Synthesis of Polyimide (P-12)

Under a dry nitrogen flow, 27.47 g (0.075 mol) of BAHF, 1.24 g (0.0050 mol) of SiDA, 5.35 g (0.010 mol) of Priamine 1075 as an end-capping agent, 2.18 g (0.020 mol) of MAP and 150.00 g of NMP were weighed and dissolved in a three-necked flask. Into this, a solution in which 31.02 g (0.10 mol) of ODPA was dissolved in 50.00 g of NMP was added. The resultant solution was stirred at 20° C. for one hour and then stirred at 50° C. for four hours. Thereafter, 15 g of xylene was added to the solution, and the resultant solution was stirred at 150° C. for five hours while azeotropically distilling water together with xylene. After completion of the reaction, the reaction solution was introduced into 3 L of water, and precipitated solid precipitates were collected by filtration. The obtained solid material was washed with water three times and was then dried with a vacuum dryer at 80° C. for 24 hours to produce a polyimide (P-12).

Example 3

Under a yellow light, 10.00 g of BMI-689, 10.00 g of polyimide resin (P-1), 0.50 g of NCI-831, 0.10 g of IRGANOX 3114, and 0.30 g of 3-trimethoxysilyl phthalamic acid were dissolved in 20.00 g of NMP, and 0.10 g of 1% by mass EL solution of Polyflow 77 was added and stirred to obtain a varnish. For the characteristics of the obtained varnish, the patternability, the dielectric constant, the dissipation factor, the glass transition point, and the elongation at break were measured by the evaluation methods described above.

Example 4

The procedure was performed in the same manner as in Example 3 except that BMI-689 was changed to U-847.

Example 5

Under a yellow light, 10.00 g of M-1, 10.00 g of a polyamide resin (P-2), 0.50 g of NCI-831, 0.10 g of IRGANOX 3114, and 0.30 g of 3-trimethoxysilyl phthalamic acid were dissolved in 20.00 g of NMP, and 0.10 g of 1% by mass EL solution of Polyflow 77 was added and stirred to obtain a varnish. The characteristics of the obtained varnish were measured in the same manner as in Example 3.

Example 6

The procedure was performed in the same manner as that in Example 5 except that P-2 was replaced with P-3.

Example 7

The procedure was performed in the same manner as that in Example 5 except that P-2 was replaced with P-4.

Example 8

The procedure was performed in the same manner as that in Example 5 except that P-2 was replaced with P-5.

Example 9

The procedure was performed in the same manner as that in Example 5 except that P-2 was replaced with P-6.

Example 10

The procedure was performed in the same manner as that in Example 5 except that P-2 was replaced with MEHC-7851SS.

Example 11

The procedure was performed in the same manner as that in Example 5 except that CYCLOTENE4026-46 was replaced with P-2.

Example 12

Under a yellow light, 10.00 g of M-1, 10.00 g of XIRAN2000, 0.50 g of NCI-831, 0.10 g of IRGANOX 3114, and 0.30 g of 3-trimethoxysilyl phthalamic acid were dissolved in 20.00 g of toluene, and 0.10 g of 1% by mass EL solution of Polyflow 77 was added and stirred to obtain a varnish. The characteristics of the obtained varnish were measured in the same manner as in Example 3.

Example 13

The procedure was performed in the same manner as in Example 12 except that XIRAN2000 was replaced with APL6015T.

Example 14

The procedure was performed in the same manner as that in Example 5 except that P-2 was replaced with P-1.

Example 15

The procedure was performed in the same manner as in Example 14 except that M-1 was replaced with M-2.

Example 16

The procedure was performed in the same manner as that in Example 5 except that P-2 was replaced with P-7.

Example 17

The procedure was performed in the same manner as that in Example 5 except that P-2 was replaced with P-8.

Example 18

The procedure was performed in the same manner as that in Example 5 except that P-2 was replaced with P-9.

Example 19

The procedure was performed in the same manner as that in Example 5 except that P-2 was replaced with P-10.

Example 20

The procedure was performed in the same manner as that in Example 5 except that P-2 was replaced with P-11.

Example 21

The procedure was performed in the same manner as that in Example 5 except that P-2 was replaced with P-12.

Example 22

The procedure was performed in the same manner as that in Example 5 except that 10.00 g of P-2 was replaced with 8.00 g of P-12 and 2.00 g of MEHC-7851SS.

Example 23

2.00 g of VG-3101 was added to Example 22, and the procedure was performed in the same manner as in Example 22.

Example 24

2.00 g of OXT-121 was added to Example 22, and the procedure was performed in the same manner as in Example 22.

Example 25

2.00 g of MOM was added to Example 22, and the procedure was performed in the same manner as in Example 22.

Comparative Example 1

Under a yellow light, 10.00 g of P-1, 10.00 g of DCP-A, 0.50 g of NCI-831, 0.10 g of IRGANOX 3114, 0.30 g of 3-trimethoxysilyl phthalamic acid, and 2.00 g of MOM were dissolved in 27.00 g of NMP, and 0.10 g of 1% by mass EL solution of Polyflow 77 was added and stirred to obtain a varnish. For the characteristics of the obtained varnish, the patternability, the dielectric constant, the dissipation factor, the glass transition point, and the elongation at break were measured by the evaluation methods described above.

TABLE 2

| | Varnish composition excluding solvent (parts by mass) | | | | |
|---|---|---|---|---|---|
| | Polyfunctional monomer (A) | Binder resin (B) | Photopolymerization initiator (C) | Crosslinking agent (D) | Other components |
| Example 3 | BMI-689 (100) | P-1(100) | NCI-831(5) | — | IRGANOX 3114 (1)<br>3-Trimethoxysilyl phthalamic acid (3)<br>Polyflow 77 (0.01) |

TABLE 2-continued

| | Varnish composition excluding solvent (parts by mass) | | | | |
|---|---|---|---|---|---|
| | Polyfunctional monomer (A) | Binder resin (B) | Photopolymerization initiator (C) | Crosslinking agent (D) | Other components |
| Example 4 | U-847(100) | P-1(100) | NCI-831(5) | — | IRGANOX 3114 (1)<br>3-Trimethoxysilyl phthalamic acid (3)<br>Polyflow 77 (0.01) |
| Example 5 | M-1(100) | P-2(100) | NCI-831(5) | — | IRGANOX 3114 (1)<br>3-Trimethoxysilyl phthalamic acid (3)<br>Polyflow 77 (0.01) |
| Example 6 | M-1(100) | P-3(100) | NCI-831(5) | — | IRGANOX 3114 (1)<br>3-Trimethoxysilyl phthalamic acid (3)<br>Polyflow 77 (0.01) |
| Example 7 | M-1(100) | P-4(100) | NCI-831(5) | — | IRGANOX 3114 (1)<br>3-Trimethoxysilyl phthalamic acid (3)<br>Polyflow 77 (0.01) |
| Example 8 | M-1(100) | P-5(100) | NCI-831(5) | — | IRGANOX 3114 (1)<br>3-Trimethoxysilyl phthalamic acid (3)<br>Polyflow 77 (0.01) |
| Example 9 | M-1(100) | P-6(100) | NCI-831 (5) | — | IRGANOX 3114 (1)<br>3-Trimethoxysilyl phthalamic acid (3)<br>Polyflow 77 (0.01) |
| Example 10 | M-1(100) | MEHC-7851SS (100) | NCI-831(5) | — | IRGANOX 3114 (1)<br>3-Trimethoxysilyl phthalamic acid (3)<br>Polyflow 77 (0.01) |
| Example 11 | M-1(100) | CYCLOTENE4026-46 (100) | NCI-831(5) | — | IRGANOX 3114 (1)<br>3-Trimethoxysilyl phthalamic acid (3)<br>Polyflow 77 (0.01) |
| Example 12 | M-1(100) | XIRAN2000 (100) | NCI-831(5) | -— | IRGANOX 3114 (1)<br>3-Trimethoxysilyl phthalamic acid (3)<br>Polyflow 77 (0.01) |
| Example 13 | M-1(100) | APL6015T (100) | NCI-831(5) | — | IRGANOX 3114 (1)<br>3-Trimethoxysilyl phthalamic acid (3)<br>Polyflow 77 (0.01) |
| Example 14 | M-1(100) | P-1(100) | NCI-831(5) | — | IRGANOX 3114 (1)<br>3-Trimethoxysilyl phthalamic acid (3)<br>Polyflow 77 (0.01) |

TABLE 3

| | Varnish composition excluding solvent (parts by mass) | | | | |
|---|---|---|---|---|---|
| | Polyfunctional monomer (A) | Binder resin (B) | Photopolymerization initiator (C) | Crosslinking agent (D) | Other components |
| Example 15 | M-2(100) | P-1(100) | NCI-831(5) | — | IRGANOX 3114 (1)<br>3-Trimethoxysilyl phthalamic acid (3)<br>Polyflow 77 (0.01) |
| Example 16 | M-1(100) | P-7(100) | NCI-831 (5) | — | IRGANOX 3114 (1)<br>3-Trimethoxysilyl phthalamic acid (3)<br>Polyflow 77 (0.01) |
| Example 17 | M-1(100) | P-8(100) | NCI-831 (5) | — | IRGANOX 3114 (1)<br>3-Trimethoxysilyl phthalamic acid (3)<br>Polyflow 77 (0.01) |
| Example 18 | M-1(100) | P-9(100) | NCI-831 (5) | — | IRGANOX 3114 (1)<br>3-Trimethoxysilyl phthalamic acid (3)<br>Polyflow 77 (0.01) |
| Example 19 | M-1(100) | P-10(100) | NCI-831 (5) | — | IRGANOX 3114 (1)<br>3-Trimethoxysilyl phthalamic acid (3)<br>Polyflow 77 (0.01) |
| Example 20 | M-1(100) | P-11(100) | NCI-831 (5) | — | IRGANOX 3114 (1)<br>3-Trimethoxysilyl phthalamic acid (3)<br>Polyflow 77 (0.01) |
| Example 21 | M-1(100) | P-12(100) | NCI-831 (5) | — | IRGANOX 3114 (1)<br>3-Trimethoxysilyl phthalamic acid (3)<br>Polyflow 77 (0.01) |
| Example 22 | M-1(100) | P-11(80)<br>MEHC-7851SS (20) | NCI-831 (5) | — | IRGANOX 3114 (1)<br>3-Trimethoxysilyl phthalamic acid (3)<br>Polyflow 77 (0.01) |
| Example 23 | M-1(100) | P-11(80)<br>MEHC-7851SS (20) | NCI-831 (5) | VG-3101 (20) | IRGANOX 3114 (1)<br>3-Trimethoxysilyl phthalamic acid (3)<br>Polyflow 77 (0.01) |
| Example 24 | M-1(100) | P-11(80)<br>MEHC-7851SS (20) | NCI-831 (5) | OXT-121 (20) | IRGANOX 3114 (1)<br>3-Trimethoxysilyl phthalamic acid (3)<br>Polyflow 77 (0.01) |

TABLE 3-continued

| | Varnish composition excluding solvent (parts by mass) | | | | |
|---|---|---|---|---|---|
| | Polyfunctional monomer (A) | Binder resin (B) | Photopolymerization initiator (C) | Crosslinking agent (D) | Other components |
| Example 25 | M-1(100) | P-11(80)<br>MEHC-7851SS (20) | NCI-831 (5) | MOM(20) | IRGANOX 3114 (1)<br>3-Trimethoxysilyl phthalamic acid (3)<br>Polyflow 77 (0.01) |
| Comparative Example 1 | DCP-A(100) | P-1(100) | NCI-831 (5) | MOM(20) | IRGANOX 3114 (1)<br>3-Trimethoxysilyl phthalamic acid (3)<br>Polyflow 77 (0.01) |

TABLE 4

| | Evaluation results | | | | | | | | | | |
|---|---|---|---|---|---|---|---|---|---|---|---|
| | | | Patternability | | Dielectric properties (1 GHz) | | | Heat resistance | | Elongation at break | |
| | Developer | Rinse solution | Develop-ability | Sensitivity | Dielectric constant | Dissipation factor | Evaluation | Glass transition point (° C.) | Evaluation | Elongation (%) | Evaluation |
| Example 3 | CP | IPA | B | C | 2.7 | 0.005 | A | 140 | D | 40 | A |
| Example 4 | TMAH | $H_2O$ | A | A | 3.0 | 0.009 | B | 150 | C | 40 | A |
| Example 5 | CP | IPA | A | A | 3.1 | 0.007 | B | 110 | D | 200 | A |
| Example 6 | CP | IPA | A | A | 3.1 | 0.006 | B | 110 | D | 200 | A |
| Example 7 | CP | IPA | A | A | 3.0 | 0.005 | B | 120 | D | 120 | A |
| Example 8 | TMAH | $H_2O$ | A | A | 2.7 | 0.005 | A | 120 | D | 5 | C |
| Example 9 | TMAH | $H_2O$ | A | A | 2.9 | 0.011 | B | 100 | D | 5 | C |
| Example 10 | TMAH | $H_2O$ | A | A | 2.9 | 0.004 | A | 110 | D | 5 | C |
| Example 11 | Dipropylene glycol dimethyl ether 30% KC cleaner NX 70% | IPA | A | A | 2.6 | 0.003 | A | 160 | C | 5 | C |
| Example 12 | Toluene | IPA | A | A | 2.9 | 0.004 | A | 120 | D | 30 | A |
| Example 13 | Toluene | IPA | A | A | 2.5 | 0.002 | A | 100 | D | 5 | C |
| Example 14 | TMAH | $H_2O$ | A | A | 2.8 | 0.005 | A | 160 | C | 40 | A |
| Example 15 | TMAH | $H_2O$ | A | A | 2.9 | 0.009 | A | 160 | C | 30 | A |
| Example 16 | CP | IPA | A | A | 2.9 | 0.007 | A | 160 | C | 40 | A |
| Example 17 | CP | IPA | A | A | 2.9 | 0.004 | A | 140 | C | 50 | A |
| Example 18 | TMAH | $H_2O$ | A | A | 3.0 | 0.006 | B | 170 | B | 40 | A |
| Example 19 | CP | IPA | A | A | 2.9 | 0.007 | A | 150 | C | 40 | A |
| Example 20 | TMAH | $H_2O$ | A | A | 2.9 | 0.009 | A | 150 | C | 40 | A |
| Example 21 | TMAH | $H_2O$ | A | A | 2.8 | 0.005 | A | 150 | C | 50 | A |
| Example 22 | TMAH | $H_2O$ | A | A | 2.8 | 0.004 | A | 140 | C | 50 | A |
| Example 23 | TMAH | $H_2O$ | A | A | 3.1 | 0.009 | B | 200 | A | 40 | A |
| Example 24 | TMAH | $H_2O$ | A | A | 3.2 | 0.009 | B | 170 | B | 60 | A |
| Example 25 | TMAH | $H_2O$ | A | A | 2.9 | 0.007 | A | 210 | A | 50 | A |
| Comparative Example 1 | TMAH | $H_2O$ | A | A | 3.5 | 0.023 | E | 240 | A | 60 | A |

DESCRIPTION OF REFERENCE SIGNS

1*a*: Cross-sectional view
1*b*: Top view
11: Antenna unit
12: Matching circuit
13: MSL feeding line
14: Feeding point
15: Ground
16: Insulation film
J: Ground wiring thickness
K: Antenna wiring thickness
L: Length of antenna unit
M: Length of matching circuit
W: Width of antenna unit
201: IC chip
202: Electrode pad
203: Second via wiring
204: Planar antenna wiring
205: Second sealing resin
206: Ground
207: First via wiring
208: First sealing resin
209: Copper wiring
210: Insulation film
211: Barrier metal
212: Solder bump

The invention claimed is:

1. A photosensitive resin composition comprising a polyfunctional monomer (A), a binder resin (B), and a photopolymerization initiator (C), wherein the polyfunctional monomer (A) contains a compound represented by expression (1) and/or a compound represented by expression (2), and the binder resin (B) contains one or more substance selected from the group consisting of a polyimide, a polyimide precursor, a polybenzoxazole, a polybenzoxazole precursor, a polyamide, a copolymer thereof, a polyurea, a polyester, a polysiloxane, an acrylic resin, a phenol resin, a benzocyclobutene resin, a maleic acid resin, and a cycloolefin polymer,

[Chem. 1]

(1)

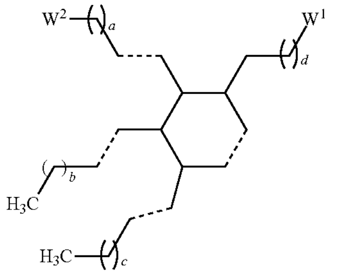

wherein, in expression (1), $W^1$ and $W^2$ each independently represent a monovalent organic group having a carbon-carbon double bond and 2 to 25 carbon atoms, and a, b, c, and d are natural numbers each independently satisfying a+b=6 to 17 and c+d=8 to 19, and the broken line part means a carbon-carbon single bond or a carbon-carbon double bond,

[Chem. 2]

(2)

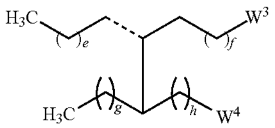

in expression (2), $W^3$ and $W^4$ each independently represent a monovalent organic group having a carbon-carbon double bond and 2 to 25 carbon atoms, and e, f, g, and h are each independently a natural number satisfying e+f=5 to 16 and g+h=8 to 19, and the broken line part means a carbon-carbon single bond or a carbon-carbon double bond, wherein, in expression (1) and expression (2), at least one of $W^1$ and $W^2$, and at least one of $W^3$ and $W^4$, are groups represented by expression (3) or expression (4),

[Chem. 3]

(3)

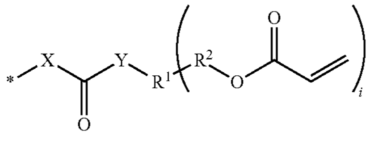

(4)

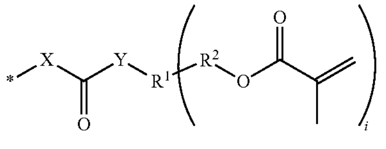

wherein, in expression (3) and expression (4), X and Y represent —NH—, $R^1$ represents a single bond or a 2 to 6 valent organic group having 1 to 5 carbon atoms, $R^2$ represents a single bond or a divalent organic group having 1 to 5 carbon atoms i represents an integer 1 to 5, and a sign of * indicates a point of bonding.

2. The photosensitive resin composition according to claim 1, wherein in expression (1) and expression (2), at least one of $W^1$ and $W^2$ and at least one of $W^3$ and $W^4$ are groups represented by expression (8), expression (9), expression (10) or expression (11),

[Chem. 5]

(8)

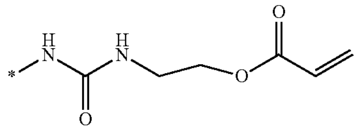

(9)

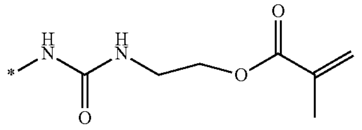

[Chem. 6]

(10)

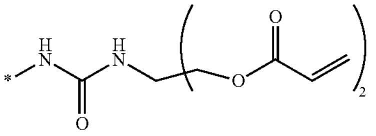

(11)

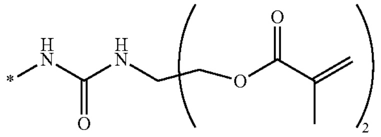

wherein a sign of * indicates a point of bonding.

3. The photosensitive resin composition according to claim 1, wherein the binder resin (B) contains one or more substance selected from the group consisting of a polyimide, a polyimide precursor, a polybenzoxazole, a polybenzoxazole precursor, a copolymer thereof, and a maleic acid resin.

4. The photosensitive resin composition according to claim 3, wherein the binder resin (B) contains one or more substance selected from the group consisting of a polyimide, a polyimide precursor, a polybenzoxazole, a polybenzoxazole precursor, and a copolymer thereof, which are obtained by polymerizing a dimer acid derivative as a monomer.

5. The photosensitive resin composition according to claim 3, wherein the binder resin (B) further contains a phenol resin having a biphenyl structure.

6. The photosensitive resin composition according to claim 1, wherein the photosensitive resin composition further contains a crosslinking agent (D), and the crosslinking agent (D) contains one or more substance selected from the group consisting of an epoxy compound, an oxetane compound, and a methylol compound.

7. The photosensitive resin composition according to claim 6, wherein the crosslinking agent (D) contains a methylol compound.

8. A cured film obtained by curing the photosensitive resin composition according to claim 1.

9. An electronic component comprising the cured film according to claim 8.

10. An antenna element comprising at least one antenna wiring and the cured film according to claim 8, wherein the antenna wiring includes at least one selected from the group consisting of a meander-shaped loop antenna, a coil-shaped loop antenna, a meander-shaped monopole antenna, a meander-shaped dipole antenna, or a planar antenna, an occupied area per antenna unit in the antenna wiring is 1000 $mm^2$ or less, and the cured film is an insulation film that insulates between a ground and the antenna wiring.

11. A semiconductor package comprising at least a semiconductor element, a rewiring layer, a sealing resin, and an antenna wiring, wherein the antenna wiring includes at least one or more selected from the group consisting of a meander-shaped loop antenna, a coil-shaped loop antenna, a meander-shaped monopole antenna, a meander-shaped dipole antenna, and a microstrip antenna, an occupied area per antenna unit in the antenna wiring is 1000 $mm^2$ or less, an insulating layer of the rewiring layer and/or the sealing resin includes the cured film according to claim 8, and the sealing resin is between a ground and the antenna wiring.

12. An electronic component comprising a cured film obtained by curing the photosensitive resin composition according to claim 1 which comprises:

an antenna wiring; and an antenna element obtained by laminating the cured film, wherein the antenna wiring has a height of 50 to 200 μm, and the cured film has a thickness of 80 to 300 μm.

13. A compound represented by expression (1) or a compound represented by expression (2),

[Chem. 7]

(1)

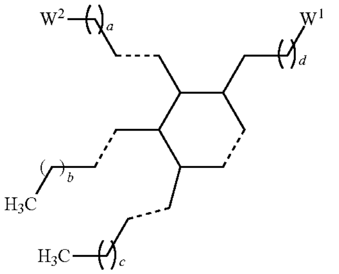

wherein, in expression (1), $W^1$ and $W^2$ each independently represent a group represented by expression (3) or expression (4), and a, b, c, and d are natural numbers each independently satisfying a+b=6 to 17 and c+d=8 to 19, and the broken line part means a carbon-carbon single bond or a carbon-carbon double bond;

[Chem. 8]

(2)

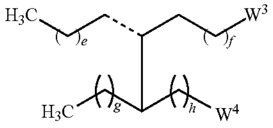

in expression (2), $W^3$ and $W^4$ each independently represent a group represented by expression (3) or expression (4), and e, f, g, and h are each independently a natural number satisfying e+f=5 to 16 and g+h=8 to 19, and the broken line part means a carbon-carbon single bond or a carbon-carbon double bond;

[Chem. 20]

(3)

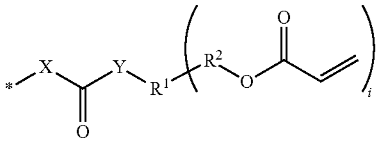

(4)

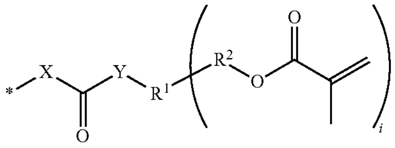

in expression (3) and expression (4), X and Y represent —NH—, $R^1$ represents a single bond or a 2 to 6 valent organic group having 1 to 5 carbon atoms, $R^2$ represents a single bond or a divalent organic group having 1 to 5 carbon atoms, i represents an integer 1 to 5, and a sign of indicates a point of bonding.

* * * * *